United States Patent
Goodman et al.

(10) Patent No.: US 6,861,228 B2
(45) Date of Patent: Mar. 1, 2005

(54) MODULATING ROBO: LIGAND INTERACTIONS

(75) Inventors: Corey S. Goodman, Berkeley, CA (US); Thomas Kidd, Berkeley, CA (US); Katja Brose, San Francisco, CA (US); Marc Tessier-Lavigne, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/289,776

(22) Filed: Nov. 6, 2002

(65) Prior Publication Data

US 2003/0170727 A1 Sep. 11, 2003

Related U.S. Application Data

(60) Continuation of application No. 09/922,600, filed on Aug. 3, 2001, now abandoned, which is a continuation of application No. 09/540,245, filed on Mar. 31, 2000, now Pat. No. 6,270,984, which is a division of application No. 09/191,647, filed on Nov. 13, 1998, now Pat. No. 6,046,015.
(60) Provisional application No. 60/081,057, filed on Apr. 7, 1998, and provisional application No. 60/065,544, filed on Nov. 14, 1997.

(51) Int. Cl.[7] ..................... G01N 33/53; A61K 39/395; C07K 16/18
(52) U.S. Cl. ................. 435/7.1; 424/139.1; 530/387.1; 530/387.9
(58) Field of Search .......................... 530/387.1, 387.9; 435/7.1; 424/139.1

(56) References Cited

FOREIGN PATENT DOCUMENTS

WO    WO-92/10518    *   6/1992

OTHER PUBLICATIONS

Rothberg et al., 1990, Genes & Devel. 4:2169–87.

Wilson et al., Nature, vol. 368: pp. 32–38. (Mar. 3, 1994).

Hillier et al., Locus AA055976 of the Embl–est58 and Genbank–est111 databases, unnumbered page (Feb. 1, 1997).

Hillier et al., Locus R78732 of the Embl–est58 and Genbank–est111 databases, unnumbered page (Jun. 9, 1995).

* cited by examiner

*Primary Examiner*—Terry McKelvey
(74) *Attorney, Agent, or Firm*—Townsend and Townsend and Crew LLP

(57) ABSTRACT

Disclosed are methods and compositions for identifying agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the aget modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

31 Claims, No Drawings

MODULATING ROBO: LIGAND INTERACTIONS

This application is a continuation of and claims the benefit of U.S. application Ser. No. 09/922,600, filed Aug. 3, 2001, abandoned which is a continuation of and claims the benefit of U.S. application Ser. No. 09/540,245, filed Mar. 31, 2000, now U.S. Pat. No. 6,270,984, which is a divisional of and claims the benefit of U.S. application Ser. No. 09/191,647, filed Nov. 13, 1998, now U.S. Pat. No. 6,046,015 which claims the benefit of U.S. Provisional Application No. 60/081,057 filed Apr. 07, 1998 and U.S. Provisional Application No. 60/065,544, filed Nov. 14, 1997, all of which are incorporated herein by reference.

The research carried out in the subject application was supported in part by NIH grant NS18366. The government may have rights in any patent issuing on this application.

INTRODUCTION

Field of the Invention

The field of this invention is methods for modulating nerve cell function.

BACKGROUND

In the developing CNS, most growth cones confront the midline at one or multiple times during their journey and make the decision of whether to cross or not to cross. This decision is not a static one but rather changes according to the growth cone's history. For example, in the Drosophila ventral nerve cord, about 10% of the interneurons project their axons only on their own side, in some cases extending near the midline without crossing it. The other 90% of the interneurons first project their axons across the midline and then turn to project longitudinally on the other side, often extending near the midline. These growth cones, having crossed the midline once, never cross it again, in spite of their close proximity to the midline and the many commissural axons crossing it. This decision to cross or not to cross is not unique to Drosophila but is common to a variety of midline structures in all bilaterally symmetric nervous systems.

What midline signals and growth cone receptors control whether growth cones do or do not cross the midline? After crossing once, what mechanism prevents these growth cones from crossing again? A related issue concerns the nature of the midline as an intermediate target. If so many growth cones find the midline such an attractive structure, why do they cross over it rather than linger? Why do they leave the midline?

One approach to find the genes encoding the components of such a system is to screen for mutations in which either too many or too few axons cross the midline. Such a large-scale mutant screen was previously conducted in Drosophila, and led to the identification of two key genes: commissureless (comm) and roundabout (robo) (Seeger et al., 1993; reviewed by Tear et al., 1993). In comm mutant embryos, commissural growth cones initially orient toward the midline but then fail to cross it and instead recoil and extend on their own side. robo mutant embryos, on the other hand, display the opposite phenotype in that too many axons cross the midline; many growth cones that normally extend only on their own side instead now project across the midline and axons that normally cross the midline only once instead appear to cross and recross multiple times (Seeger et al, 1993; present disclosure). Double mutants of comm and robo display a robo-like phenotype.

How do comm and robo function to control midline crossing? Neither the initial paper on these genes (Seeger et al., 1993) nor the cloning of comm (Tear et al., 1996) resolved this question. comm encodes a novel surface protein expressed on midline cells. In fact, the comm paper (Tear et al., 1996) ended with the hope that future work would " . . . help shed some light on the enigmatic function of Comm."

U.S. Ser. No. 08/971,172 (Robo, A Novel Family of Polypeptides and Nucleic Acids, by inventors: Corey S. Goodman, Thomas Kidd, Kevin J. Mitchell and Guy Tear, now abandoned) discloses the cloning and characterization of robo in various species including Drosophila; Robo polypeptides and polypeptide-encoding nucleic acids are also disclosed and their genbank accession numbers referenced in Kidd et al. (1998) Cell 92, 205–215. robo encodes a new class of guidance receptor with 5 immunoglobulin (Ig) domains, 3 fibronectin type III domains, a transmembrane domain, and a long cy subfamily of Ig superfamily proteins that is highly conserved from fruit flies to mammals. The Robo ectodomains, and in particular the first two Ig domains, are highly conserved from fruit fly to human, while the cytoplasmic domains are more divergent. Nevertheless, the cytoplasmic domains contain three highly conserved short proline-rich motifs which may represent binding sites for SH3 or other binding domains in linker or signaling molecules.

For those axons that never cross the midline, Robo is expressed on their growth cones from the outset; for the majority of axons that do cross the midline, Robo is expressed at high levels on their growth cones only after they cross the midline. Transgenic rescue experiments in Drosophila reveal that Robo can function in a cell autonomous fashion, consistent with it functioning as a receptor. Thus, in Drosophila, Robo appears to function as the gatekeeper controlling midline crossing; growth cones expressing high levels of Robo are prevented from crossing the midline. Robo proteins in mammals function in a similar manner in controlling axon guidance.

U.S. Ser. No. 60/065,54 (Methods for Modulating Nerve Cell Function, by inventors: Corey S. Goodman, Thomas Kidd, Guy Tear, Claire Russell and Kevin Mitchell) discloses ectopic and overexpression studies revealing that Comm down-regulates Robo expression, demonstrating that Comm functions to suppress the Robo-mediated midline repulsion. These results show that the levels of Comm at the midline and Robo on growth cones are tightly intertwined and dynamically regulated to assure that only certain growth cones cross the midline, that those growth cones that cross do not linger at the midline, and that once they cross they never do so again.

Relevant Literature

Seeger, M., Tear, G., Ferres-Marco, D. and Goodman C. S. (1993) Neuron 10,409–426; Tear G., et al. (1996) Neuron 16, 501–514; Rothberg et al. (1990) Genes Dev 4, 2169–2187; Kidd et al. (1998) Cell 92, 205–215.

SUMMARY OF THE INVENTION

The invention provides methods and compositions relating to vertebrate Slit1 and Slit2, collectively vertebrate Slit) polypeptides, related nucleic acids, polypeptide domains thereof having vertebrate Slit-specific structure and activity, and modulators of vertebrate Slit function. Vertebrate Slit polypeptides can regulate cell, especially nerve cell, function and morphology. The polypeptides may be produced recombinantly from transformed host cells from the subject vertebrate Slit polypeptide encoding nucleic acids or purified from mammalian cells. The invention provides isolated vertebrate Slit hybridization probes and primers capable of specifically hybridizing with natural vertebrate Slit genes, vertebrate Slit-specific binding agents such as specific antibodies, and methods of making and using the subject compositions in diagnosis (e.g. genetic hybridization screens for vertebrate Slit transcripts), therapy (e.g. to modulate nerve cell growth) and in the biopharmaceutical industry (e.g. as immunogens, reagents for isolating vertebrate Slit genes and polypeptides, reagents for screening chemical libraries for lead pharmacological agents, etc.).

The invention also provides methods and compositions for identifying agents which modulate the interaction of Robo and a Robo ligand and for modulating the interaction of Robo and a Robo ligand. The methods for identifying Robo:ligand modulators find particular application in commercial drug screens. These methods generally comprise (1) combining a Robo polypeptide, a Slit polypeptide and a candidate agent under conditions whereby, but for the presence of the agent, the Robo and Slit polypeptides engage in a first interaction, and (2) determining a second interaction of the Robo and Slit polypeptides in the presence of the agent, wherein a difference between the first and second interactions indicates that the aget modulates the interaction of the Robo and Slit polypeptides. The subject methods of modulating the interaction of Robo and a Robo ligand involve combining a Robo polypeptide, a Slit polypeptide and a modulator under conditions whereby, but for the presence of the modulator, the Robo and Slit polypeptides engage in a first interaction, whereby the Robo and Slit polypeptides engage in a second interaction different from the first interaction. In a particular embodiment, the modulator is dominant negative form of the Robo or Slit polypeptide.

DETAILED DESCRIPTION OF THE INVENTION

The subject methods include screens for agents which modulate Robo:ligand interactions and methods for modulating Robo:ligand interactions. Robo activation is found to regulate a wide variety of cell functions, including cell-cell interactions, cell mobility, morphology, etc. Slit polypeptides are disclosed as specific activators and inactivators of Robo polypeptides. Accordingly, the invention provides methods for modulating targeted cell function comprising the step of modulating Robo activation by contacting the cell with a modulator of a Robo:Slit interaction.

The targeted Robo polypeptide is generally naturally expressed on the targeted cells. The nucleotide sequences of exemplary natural cDNAs encoding *drosophila* 1, *drosophila* 2, C. elegans, human 1, human 2 and mouse 1 Robo polypeptides and their translates are described in Kidd et al. (1998) Cell 92, 205–215 and U.S. Ser. No. 08/971,172. The targeted Robo polypeptides comprise at least a functional Robo domain, which domain has Robo-specific amino acid sequence and binding specificity or function. Preferred Robo domains comprise at least 8, preferably at least 16, more preferably at least 32, most preferably at least 64 consecutive residues of a natural full length Robo. In a particular embodiment, the domains comprise one or more structural/functional Robo immunoglobulin, fibronectin or cytoplasmic motif domains described herein. The subject domains provide Robo-specific antigens and/or immunogens, especially when coupled to carrier proteins. For example, peptides corresponding to Robo- and human Robo-specific domains are covalently coupled to keyhole limpet antigen (KLH) and the conjugate is emulsified in Freunds complete adjuvant. Laboratory rabbits are immunized according to conventional protocol and bled. The presence of Robo-specific antibodies is assayed by solid phase immunosorbant assays using immobilized Robo polypeptides. Generic Robo-specific peptides are readily apparent as conserved regions in aligned Robo polypeptide sequences. In addition, species-specific antigenic and/or immunogenic peptides are readily apparent as diverged extracellular or cytosolic regions in alignments Human Robo-specific antibodies are characterized as uncross-reactive with non-human Robo polypeptides.

The subject domains provide Robo domain specific activity or function, such as Robo-specific cell, especially neuron modulating or modulating inhibitory activity, Robo-ligand-binding or binding inhibitory activity. Robo-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Robo regulating protein or other regulator that directly modulates Robo activity or its localization; or non-natural binding target such as a specific immune protein such as an antibody, or a Robo specific agent such as those identified in screening assays such as described below. Robo-binding specificity may be assayed by binding equilibrium constants (usually at least about $10^7 M^{-1}$, preferably at least about $10^8 M^{-1}$, more preferably at least about $10^9 M^{-1}$), by the ability of the subject polypeptide to function as negative mutants in Robo-expressing cells, to elicit Robo specific antibody in a heterologous host (e.g a rodent or rabbit), etc.

Similarly, the Slit polypeptide is conveniently selected from Slit polypeptides which specifically activate or inhibit the activation of the Robo polypeptide. Exemplary suitable Slit polypeptides (a) comprises a vertebrate Slit sequence disclosed herein, especially human Slit-1 (SEQ ID NO:02), or a deletion mutant thereof which specifically modulates Robo expression or a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural *drosophila* Slit sequence, preferably other than a natural invertebrate Slit sequence, and/or (b) is encoded by a nucleic acid comprising a natural Slit encoding sequence (such as a natural human Slit-1 encoding sequence, SEQ ID NO:01) or a fragment thereof at least 36, preferably at least 72, more preferably at least 144, most preferably at least 288 nucleotides in length which specifically hybridizes thereto. Suitable deletion mutants are readily screened in Robo binding or activation assays as described herein. Preferred Slit domains/deletion mutants/fragments comprise at least 8, preferably at least 16, more preferably at least 32, most preferably at least 64 consecutive residues of a disclosed vertebrate Slit sequences and provide a Slit specific activity, such as Slit-specific antigenicity and/or immunogenicity, especially when coupled to carrier proteins as described above for Robo above. Suitable natural Slit encoding sequence fragments are of length sufficient to encode such Slit domains. In a particular embodiment, the Slit fragments comprise species specific fragments; such fragments are readily discerned from alignments of the disclosed sequences, see, e.g. shown as unboxed sequences in Tables 1 and 2.

TABLE 1

Alignment of human Slit-1 (SEQ ID NO:02), human Slit-2 (SEQ ID NOS:03–06), Drosophila Slit-1 (SEQ ID NO:07), C. elegans Slit-1 (SEQ ID NOS:08–09), mouse Slit-2 (SEQ ID NOS:10–11) and mouse Slit-1 (SEQ ID NOS:12–14).

```
  1  M A A P S R T T L M P P P F R L Q L R L - L I L P T L L L L R H D A V H A E P Y   D-Slit
  1  M R G V G W Q - - - - - - - M L S L S L G L V L A I L - - - - - - - - - - - - -   H-Slit1

40  S G G F G S S A V S S G G L G S V G I H I P G G G V G V I T E A R C P R V C S C   D-Slit
 21  - - - - - - - - - - - - - - - - - - - - - - - - - N K V A P Q A C P A Q C S C   H-Slit1

80  T G L N V D C S H R G L T S V P R K I S A D V E R L E L Q G N N L T V I Y E T D   D-Slit
 35  S G S T V D C H G L A L R S V P R N I P R N T E R L D L N G N N I T R I T K T D   H-Slit1

120  F Q R L T K L R M L Q L T D N Q I H T I E R N S F Q D L V S L E R L - - - - - -   D-Slit
 75  F A G L R H L R V L Q L M E N K I S T I E R G A F Q D L K E L E R L R L N R N H   H-Slit1
  1  - - - - - H L R V L Q L M E N R I S T I E R G A F Q D L K E L E R L R L N R N N   M-Slit1

154  - - - - - - - - - - - - - - - D I S N N V I T T V G R V F K G A Q S L R           D-Slit
115  L Q L F P E L L F L G T A K L Y R L D L S E N Q I Q A I P R K A F R G A V D I K   H-Slit1
 36  L Q L F P E L L F L G T A R L Y R L D L S E N Q I Q A I P R K A F R G A V D I K   M-Slit1

176  S L Q L D N N Q I T C L D E H A F K G L V E L E I L T L N N N L T S L P H N I     D-Slit
155  N L Q L D Y N Q I S C I E D G A F R A L R D L E V L T L N N N N I T R L S V A S   H-Slit1
 76  N L Q L D Y N Q I S C I E D G A F R A L R D L E V L T L N N N N I T R L S V A S   M-Slit1

216  F G G L G R L R A L R L S D N P F A C D C H L S W L S R F L R S A T R L A P Y T   D-Slit
195  F N H M P K L R T F R L H S N N L Y C D C H L A W L S D W L R K R P R V G L Y T   H-Slit1
116  F N H M P K L R T F R L H S N N L Y C                                             M-Slit1

256  R C Q S P S Q L K G Q N V A D L H D Q E F K C S G L T E - H A P M - - - E C G A   D-Slit
235  Q C M G P S H L R G H N V A E V Q K R E F V C S D E E E G H Q S F M A P S C S V   H-Slit1

292  E N S C P H P C R C A D G I V D C R E K S L T S V P V T L P D D T T D V R L E Q   D-Slit
275  L H - C P A A C T C S N N I V D C R G K G L T E I P T N L P E T I T E I R L E Q   H-Slit1
  1  - - - - - S P C T C S N N I V D C R G K G L M E I P A N L P E G I V E I R L E Q   H-Slit2

332  N F I T E L P P L S F S S F R R L R R I D L S N N N I S R I A H D A L S G L K Q   D-Slit
314  N T I K V I P P G A F S P Y K K L R R I D L S N N Q I S E L A P D A F Q G L R S   H-Slit1
 36  N S I K A I P A G A F T Q Y K K L K R I D I S K N Q I S D I A P D A F Q G L K S   H-Slit2

372  L T T L V Y G N K I K D L P S G V F K G L G S L R L L L L N A N E I S C I R K     D-Slit
354  L N S L V Y G N K I T E L P K S L F E G L F S L Q L L L L N A N K I N C L R V     H-Slit1
 76  L T S L V Y G N K I T E I A K G L F D G L V S L Q L L L L                         H-Slit2

1                                                                               R   CE-Slit
412  D A F R D L H S L S L L L S L Y D N N I Q S L A N G T F D A M K S M K T V H L A K   D-Slit
394  D A F Q D L H N L N L L L S L Y D N K L Q T I A K G T F S P L R A I Q T M H L A Q   H-Slit1

2  N P X I C D C N L Q W L A Q I N L Q K N I E T S G A R C E Q P K R L R K K K F A   CE-Slit
452  N P F I C D C N L R W L A D Y L H K N P I E T S G A R C E S P K R M H R R R I E   D-Slit
434  N P F I C D C H L K W L A D Y L H T N P I E T S G A R C T S P R R L A N K R I G   H-Slit1

42  T L P P N K F K C K G S E S F V S M Y A D S C F I D S I C P T Q C D C Y G T T V   CE-Slit
492  S L R E E K F K C S - W G E L R M K L S G E C R M D S D C P A M C H C E G T T V   D-Slit
474  Q I K S K K F R C S G T E D Y R S K L S G D C F A D L A C P E K C R C E G T T V   H-Slit1

82  D C N K R G L N T I P T S I P R F A T Q L L L S G N N I S T V D L N S N I H V L   CE-Slit
531  D C T G R R L K E I P R D I P L H T T E L L L N D N E L G R I S S D G L F G R L   D-Slit
514  D C S N Q K L N K I P E H I P Q Y T A E L R L N N N E F T V L E A T G I F K K L   H-Slit1

122  E N L E X L D L S N N H I T F I N D K S F E K L S K L R E L X L N D - - - - - -   CE-Slit
571  P H L V K L E L K R N Q L T G I E P N A F E G A S H I Q E L Q L G E N K I K E I   D-Slit
554  P Q L R K I N F S N N K I T D I E E G A F E G A S G V N E I L L T S N R L E N V   H-Slit1
  1  - - - - - - - - - - - - - - - - - E G A F N G A A S V Q E L M L T G N Q L E T V   H-Slit2

611  S N K M F - - - - - - - - - - - - - - - - - - - - - - - L G L H Q L K T L N       D-Slit
594  Q H K M F K G - L E S L K T L M L R S N R I T C V G N D S F I G L S S V R L L S   H-Slit1
 24  H G R G F R G G L S G L K T L M L R S N L I G C V S N D T F A G L S S V R L L S   H-Slit2

626  L Y D N Q I S C V M P G S F E H L N S L T S L N L A S N P F N C N H L A W - F     D-Slit
633  L Y D N Q I T T V A P G A F D T L H S L S T L N L L A N P F N C N C Y L A W - L   H-Slit1
 64  L Y D N R I T T I T P G A F T T L V S L S T I N L L S N P F N C N C H L G A G L   H-Slit2
```

TABLE 1-continued

Alignment of human Slit-1 (SEQ ID NO:02), human Slit-2 (SEQ ID NOS:03–06), Drosophila
Slit-1 (SEQ ID NO:07), C. elegans Slit-1 (SEQ ID NOS:08–09), mouse Slit-2 (SEQ ID NOS:10–
11) and mouse Slit-1 (SEQ ID NOS:12–14).

```
665   A E C V R K K S L N G G A A R C G A P S K V R D V Q I K D L P H S E F K C S S E      D-Slit
672   G E W L R K K R I V T G N P R C Q K P Y F L K E I P I Q D V A I Q D F T C D D H      H-slit1
104   G K W L R K R R I V S G N P R C Q K P F F L K E I P I Q G V G H P G I                H-slit2

1                                           S N K N L T S F P S R I P F D                 CE-slit
705   N S E - G C L G D G Y C P P S C T C T G T V V A C S R N Q L K E I P R G I P A E      D-Slit
712   N D D N S C S P L S R C P T E C T C L D T V V R C S N K G L K V L P K G I P R D      H-slit1

16    T T E L Y L D A N Y I N E I P A H D L N R L Y S L T K L D L S H N R L I S L E N      CE-slit
744   T S E L Y L E S N E I E Q I H Y E R I R H L R S L T R L D L S N N Q I T I L S N      D-Slit
752   V T E L Y L D G N Q F T L V P K E - L S N Y K H L T L I D L S N N R I S T L S N      H-slit1

56    N T F S N L T R L S T L I I S Y N K L R C L Q P L A F N G L N A L R I L S L H G      CE-slit
784   Y T F A N L T K L S T L I I S Y N K L Q C L Q R H A L S G L N N L R V V S L H G      D-Slit
791   Q S F S N M T Q L L T L I L S Y N R L R C I P P R T F D G L K S L R L L S L H G      H-slit1

96    N D I S F L P Q S A F S N L T S I T H I A V G S N S L Y C D C N M A W F S K W I      CE-slit
824   N R I S M L P E G S F E D L K S L T H I A L G S N P L Y C D C G L K W F S D W I      D-Slit
831   N D I S V V P E G A F N D L S A L S H L A I G A N P L Y C D C N M Q W L S D W V      H-slit1

136   K S K F I E A G I A R C E Y P N T V S N Q L L L T A Q P Y Q F T C D S K V P T K      CE-slit
864   K L D Y V E P G I A R C A E P E Q M K D K L I L S T P S S S F V C R G R V R N D      D-Slit
871   K S E Y K E P G I A R C A G P G E M A D K L L L T T P S K K F T C Q G P V D V N      H-slit1

176   L A T K D L C L N S P C K N N A I C E T T S S R K Y T C N C T P G F Y G V H C        CE-slit
904   I L A K C N A C F E Q P C Q N Q A Q C V A L P Q R E Y Q C L C Q P G Y H G K H C      D-Slit
911   I L A K C N P C L S N P C K N D G T C N S D P V D F Y R C T C P Y G F K G Q D C      H-slit1

216   E N Q I D A C Y G S P C L N N A T C K V - - A Q A G R F N C Y C N K G F E G D Y      CE-slit
944   E F M I D A C Y G N P C R N N A T C T V - - L E E G R F S C Q C A P G Y T G A R      D-Slit
951   D V P I H A C I S N P C K H G G T C H L K E G E E D G F W C I C A D G F E G E N      H-slit1

254   C E K N I D D C V N S - K C E N G G K C V D L V R F C S E E L K N Q S F Q I N        CE-slit
982   C E T N I D D C L G E I K C Q N N A T C I D - - - - - - - - - - - - - - - G V E      D-Slit
991   C E V N V D D C - E D N D C E N N S T C V D - - - - - - - - - - - - - - - G I N      H-slit1

293   S Y R C D C P M E Y E G K H C E D K L E Y C T K K L N P C E N N G K C I P I N G      CE-slit
1007  S Y K C E C Q P G F S G E F C D T K I Q F C S P E F N P C A N G A K C M D H F T      D-Slit
1015  N Y T C L C P P E Y T G E L C E E K L D F C A Q D L N P C Q H D S K C I L T P K      H-slit1
                                                                  D P L P V              M-slit2

333   S Y S C M C S P G F T G N N C E T N I D D C K N V C Q N G G S C V D G I L S Y        CE-slit
1047  H Y S C D C Q A G F H G T N C T D N I D D C Q N H M C Q N G G T C V D G I N D Y      D-Slit
1055  G F K C D C T P G Y V G E H C D I D F D D C Q D N K C K N G A H C T D A V N G Y      H-slit1
1     - - - - - - - - - - N N D D C V G H K C R H G A Q C V D E V N G Y                   M-slit1
1     W P R C E C M P G Y A G D N C S E N Q D D C K D H K C Q N G A Q C M D E V N S Y    H-slit2
6     H H R C E C M L G Y T G D N C S E N Q D D C K D H K C Q N G A Q C V D E V N S Y    M-slit2

373   D C L C R P G Y A G Q Y C E I P P M M D M E Y Q K T D A C Q Q S A C G Q G - E C      CE-slit
1087  Q C R C P D D Y T G K Y C E G H N M I S M M Y P Q T S P C Q N H E C K H G V - C      D-Slit
1095  T C I C P E G Y S G L F C E F S P - - P M V L P R T S P C D N F D C Q N G A Q C      H-slit1
24    T C I C P Q G F S G L F C E H P P - - P M V L L Q T S P C D Q Y E C Q N G A Q C      M-slit1
41    S C L C A E G Y S G Q L C E I P P - - H L P A P K - S P C E G T E C Q N G A N C    H-slit2
46    A C L C V E G Y S G Q L C E I P P - - - - - A P R - S S C E G T E C Q N G A N C    M-slit2

412   V A S Q N - S S D F T C K C H E G F S G P S C D R Q M S V G F K N P G A Y L A L      CE-slit
1126  F Q P N A Q G S D Y L C R C H P G Y T G K W C E Y L T S I S F V H N N S F V E L      D-Slit
1133  I V R I N E P - - - I C Q C L P G Y Q G E K C E K L V S V N F I N K E S Y L Q I      H-slit1
62    I V V Q Q E P - - - T C R C P P G F A G P R C E K L I T V N F V G K D S Y V E L      M-slit1
78    V D Q G N R P - - - V C Q C L P G F G G P E C E K L L S V N F V D R D T Y L Q F    H-slit2
80    V D Q G S R P - - - V C Q C L P G F G G P E C E K L L S V N F V D R D T Y L Q F    M-slit2

451   D P L A S - - D G T I T M T L R T T S K I G I L L Y G D D H F V S A E L Y D G        CE-slit
1166  E P L R T R P E A N V T I V F S S A E Q N G I L M Y D G Q D A H L A V E L F N G      D-Slit
1170  P S A K V R P Q T N I T L Q I A T D E D S G I L L Y K G D K D H I A V E L Y R G      H-slit1
99    A S A K V R                                                                        M-slit1
115   T D L Q N W X R X N I T L Q V F T A E D N G I L L Y N G L N D H I A V X L Y X G    H-slit2
117   T D L Q N W P R A N I T L Q V S T A E D N G I L L Y N G D N D H I A V E L Y        M-slit2
```

TABLE 1-continued

Alignment of human Slit-1 (SEQ ID NO:02), human Slit-2 (SEQ ID NOS:03-06), Drosophila Slit-1 (SEQ ID NO:07), C. elegans Slit-1 (SEQ ID NOS:08-09), mouse Slit-2 (SEQ ID NOS:10-11) and mouse Slit-1 (SEQ ID NOS:12-14).

```
489   R V K L V Y Y I G N F P A S H M Y S S V K V N D G L P H R I S I R T S E R K C F   CE-Slit
1206  R I R V S Y D V G N H P V S T M Y S F E M V A D G K Y H A V E L L A I K K N F T   D-Slit
1210  R V R A S Y D T G S H P A S A I Y S V E T I N D G N F H I V E L L A L D Q S L S   H-Slit1
155   H V R F S Y                                                                       H-Slit2

529   L Q I D K N P V Q I V E N S G K S D Q L I T K G K E M L Y I G G L P I E K S Q D   CE-Slit
1246  L R V D R G L A R S I I N E G S N D Y L - - K L T T P M F L G G L P V D P A Q Q   D-Slit
1250  L S V D G G N P K I I T N L S K Q S T L - - N F D S P L Y V G G M P G K S N V A   H-Slit1
1     I L - - - - - - - - - - - - - - - - - - - - - - - - - - - - - - - - - D V A     M-Slit1

569   A K R F H V K N S E S L K G C I S S I T I N E V P I N L Q Q A L E N V N T E Q     CE-Slit
1284  A Y K N W Q I R N L T S F K G C M K E V W I N H K L V D F G N A Q R Q K I T P     D-Slit
1288  S L R Q A P G Q N G T S F H G C I R N L Y I N S E L Q D F Q K V P M Q T G I L P   H-Slit1
6     S L R Q A P G E N G T S F H G C I R N L Y I N S E L Q D F R K M P M Q T G I L P   M-Slit1

609   S C - - - - - - - - - - - - - S A T V N F - - - - - - - - - - - - - - - - - -   CE-Slit
1324  G C A L - - - - L E G E Q Q E E E D D E Q D F M D E - - - - - T P H I K E E P     D-Slit
1328  G C E P C H K K V C A H G T C Q P S S Q A G F T C E C Q E G W M G P L C D Q R T   H-Slit1
46    G C E P C H K K V C A H G C C Q P S S Q S G F T C E C E E G W M G P L C D Q R T   M-Slit1

617   - - - C A G I D C G N G - K C T N N A L S P K G Y M C Q C D S H F S G E H C D E   CE-Slit
1354  V D P C L E N K C R R G S R C V P N S N A R D G Y Q C K C K H G Q R G R Y C D Q   D-Slit
1368  N D P C L G N K C V H G T - C L P I N A F - - S Y S C K C L E G H G G V L C D E   H-Slit1
86    N D P C L G N K C V H G T - C L P I N A F - - S Y S C K C L E G H G G V L C D E   M-Slit1

653   - - - - - - - - - - - - - - - - - - - - - - - - - - - - - - - - - - - - - -   CE-Slit
1394  G E G S T E P - - - - - - - - - - - - - - - - - - - - - - P T V T A A S - -     D-Slit
1405  E E D L F N P C Q A I K C K H G K C R L S G L G Q P Y C E C S S G L Y T G D S C D H-Slit1
123   E E D L F N P C Q M I K C K H G K C R L S G V G Q P Y C E C N S G F T G D S C D   M-Slit1
1     - - - - - - - - - - - Q C H I S D Q G E P Y C L C Q P G F S G E H C Q             H-Slit2
1     - - - - - - - - - A F K C H H G Q C H I S D R G E P Y C L C Q P G F S G H H C E   M-Slit2

655   K R I K C D K Q K F R H H I E N E - - - - C R S V D R I K I A E C N G L Y C G G   CE-Slit
1405  T - - - C R K E Q V R E Y Y T E N D - - - - C R S R Q P L K Y A K C L V G G C G - D-Slit
1445  R E I S C R G E R I R D Y Y Q K Q Q G Y A A C Q T T K K V S R L E C R G G C A G   H-Slit1
163   R E I S C R G E R I R D Y Y Q K Q Q G Y A A C Q T T K K V S R L E C R G G C A G   M-Slit1
25    Q E N P C L G Q V R E V I R R Q K G Y A S C A T A S K V P I M E C R G G C - G     H-Slit2
32    Q E N P C M G E I V R E A I R R Q K D Y A S C A T A S K V P I M E C R G G C - G   M-Slit2

689   E Q N C C T A V K K Q R K V K M I C K N G T T K I S T V H I I R Q C Q C E P T     CE-Slit
1440  - N Q C C A A K I V R R R K V R M V C S N N R K Y I K N L D I V R K C G C - - T   D-Slit
1485  G Q - C C G P L R S K R R K Y S F E C T D G S S F V D E V E K V V K C G C T R -   H-Slit1
203   G Q - C C G P L R S K R R K Y S F E C T D G S S F V D E V E K V V K C G C A R -   M-Slit1
64    P Q - C C Q P T R S K R R K Y V F Q C T D G S S F V E E V E R H L E C G C L A -   H-Slit2
71    T T - C C Q P I R S K R R K Y V F Q C T D G S S F V E E V E R H L E C G C R A -   M-Slit2

729   K S V L - - S E K                                                                 CE-Slit
1477  K K C Y                                                                           D-Slit
1523  - - - - C V S                                                                     H-Slit1
241   - - - - C A S                                                                     M-Slit1
102   - - - - C - S                                                                     H-Slit2
109   - - - - C - S                                                                     M-Slit2
```

TABLE 2

Alignment of human Slit-1 (SEQ ID NO:02) and Drosophila Slit-1 (SEQ ID NO:07)

```
1    M A A P S R T T L M P P P F R L Q L R L - L I L P T L L L R H D A V H A E P Y   D-Slit
1    M R G V G W Q - - - - - - - M L S L S L G L V L A I L - - - - - - - - - - -     H-Slit1

40   S G G F G S S A V S S G G L G S V G I H I P G G G V I T E A R C P R V C S C     D-Slit
21   - - - - - - - - - - - - - - - - - - - - - - - - - N K V A P Q A C P A Q C S C   H-Slit1

80   T G L N V D C S H R G L T S V P R K I S A D V E R L E L Q G N N L T V I Y E T D D-Slit
35   S G S T V D C H G L A L R S V P R N I P R N T E R L D L N G N N I T R I T K T D H-Slit1

120  F Q R L T K L R M L Q L T D N Q I H T I E R N S F Q D L V S L E R L - - - - - - D-Slit
75   F A G L R H L R V L Q L M E N K I S T I E R G A F Q D L K E L E R L R L N R N H H-Slit1
```

TABLE 2-continued

Alignment of human Slit-1 (SEQ ID NO:02) and Drosophila Slit-1 (SEQ ID NO:07)

```
154  - - - - - - - - - - - - - - - - - - - D I S N N V I T T V G R R V F K G A Q S L R  D-Slit
115  L Q L F P E L L F L G T A K L Y R L D L S E N Q I Q A I P R K A F R G A V D I K    H-Slit1

176  S L Q L D N N Q I T C L D E H A F K G L V E L E I L T L N N N L T S L P H N I    D-Slit
155  N L Q L D Y N Q I S C I E D G A F R A L R D L E V L T L N N N I T R L S V A S    H-Slit1

216  F G G L G R L R A L R L S D N P F A C D C H L S W L S R F L R S A T R L A P Y T  D-Slit
195  F N H M P K L R T F R L H S N N L Y C D C H L A W L S D W L R K P R V G L Y T    H-Slit1

256  R C Q S P S Q L K G Q N V A D L H D Q E F K C S G L T E - H A P M - - - E C G A  D-Slit
235  Q C M G P S H L R G H N V A E V Q K R E F V C S D E E E G H Q S F M A P S C S V  H-Slit1

292  E N S C P H P C R C A D G I V D C R E K S L T S V P V T L P D D T T D V R L E Q  D-Slit
275  L H - C P A A C T C S N N I V D C R G K G L T E I P T N L P E T I T E I R L E Q  H-Slit1

332  N F I T E L P P L S F S S F R R L R R I D L S N N N I S R I A H D A L S G L K Q  D-Slit
314  N T I K V I P P G A F S P Y K K L R R I D L S N N Q I S E L A P D A F Q G L R S  H-Slit1

372  L T T L V L Y G N K I K D L P S G V F K G L G S L R L L L N A N E I S C I R K    D-Slit
354  L N S L V L Y G N K I T E L P K S L F E G L F S L Q L L L N A N K I N C L R V    H-Slit1

412  D A F R D L H S L S L L S L Y D N N I Q S L A N G T F D A M K S M K T V H L A K  D-Slit
394  D A F Q D L H N L N L L S L Y D N K L Q T I A K G T F S P L R A I Q T M H L A Q  H-Slit1

452  N P F I C D C N L R W L A D Y L H K N P I E T S G A R C E S P K R M H R R R I E  D-Slit
434  N P F I C D C H L K W L A D Y L H T N P I E T S G A R C T S P R R L A N K R I G  H-Slit1

492  S L R E E K F K C S - W G E L R M K L S G E C R M D S D C P A M C H C E G T T V  D-Slit
474  Q I K S K K F R C S G T E D Y R S K L S G D C F A D L A C P E K C R C E G T T V  H-Slit1

531  D C T G R R L K E I P R D I P L H T T E L L L N D N E L G R I S S D G L F G R L  D-Slit
514  D C S N Q K L N K I P E H I P Q Y T A E L R L N N N E F T V L E A T G I F K K L  H-Slit1

571  P H L V K L E L K R N Q L T G I E P N A F E G A S H I Q E L Q L G E N K I K E I  D-Slit
554  P Q L R K I N F S N N K I T D I E E G A F E G A S G V N E I L L T S N R L E N V  H-Slit1

611  S N K M F L G L H Q L K T L - - - - - - - - - - - - - - - - - - - - N L          D-Slit
594  Q H K M F K G L E S L K T L M L R S N R I T C V G N D S F I G L S S V R L L S L  H-Slit1

627  Y D N Q I S C V M P G S F E H L N S L T S L N L A S N P F N C N H L A W F A E    D-Slit
634  Y D N Q I T T V A P G A F D T L H S L S T L N L L A N P F N C N C Y L A W L G E  H-Slit1

667  C V R K K S L N G G A A R C G A P S K V R D V Q I K D L P H S E F K C S S E N S  D-Slit
674  W L R K K R I V T G N P R C Q K P Y F L K E I P I Q D V A I Q D F T C D D G N D  H-Slit1

707  E - G C L G D G Y C P P S C T C T G T V V A C S R N Q L K E I P R G I P A E T S  D-Slit
714  D N S C S P L S R C P T E C T C L D T V V R C S N K G L K V L P K G I P R D V T  H-Slit1

746  E L Y L E S N E I E Q I H Y E R I R H L R S L T R L D L S N N Q I T I L S N Y T  D-Slit
754  E L Y L D G N Q F T L V P K E - L S N Y K H L T L I D L S N N R I S T L S N Q S  H-Slit1

786  F A N L T K L S T L I I S Y N K L Q C L Q R H A L S G L N N L R V V S L H G N R  D-Slit
793  F S N M T Q L L T L I L S Y N R L R C I P P R T F D G L K S L R L L S L H G N D  H-Slit1

826  I S M L P E G S F E D L K S L T H I A L G S N P L Y C D C G L K W F S D W I K L  D-Slit
833  I S V V P E G A F N D L S A L S H L A I G A N P L Y C D C N M Q W L S D W V K S  H-Slit1

866  D Y V E P G I A R C A E P E Q M K D K L I L S T P S S S F V C R G R V R N D I L  D-Slit
873  E Y K E P G I A R C A G P G E M A D K L L L T T P S K K F T C Q G P V D V N I L  H-Slit1

906  A K C N A C F E Q P C Q N Q A Q C V A L P Q R E Y Q C L C P G Y H G K H C E F    D-Slit
913  A K C N O C L S N P C K N D G T C N S D P V D F Y R C T C P Y G F K G Q D C D V  H-Slit1

946  M I D A C Y G N P C R N N A T C T V L E - - E G R F S C Q C A P G Y T G A R C E  D-Slit
953  P I H A C I S N P C K H G G T C H L K E G E E D G F W C I C A D G F E G E N C E  H-Slit1

984  T N I D D C L G E I K C Q N N A T C I D G V E S Y K C E C Q P G F S G E F C D T  D-Slit
993  V N V D D C - E D N D C E N N S T C V D G I N N Y T C L C P P E Y T G E L C E E  H-Slit1
```

TABLE 2-continued

Alignment of human Slit-1 (SEQ ID NO:02) and Drosophila Slit-1 (SEQ ID NO:07)

```
1024 K I Q F C S P E F N P C A N G A K C M D H F T H Y S C D C Q A G F H G T N C T D    D-Slit
1032 K L D F C A Q D L N P C Q H D S K C I L T P K G F K C D C T P G Y V G E H C D I    H-slit1

1064 N I D D C Q N H M C Q N G G T C V D G I N D Y Q C R C P D D Y T G K Y C E G H N    D-Slit
1072 D F D D C Q D N K C K N G A H C T D A V N G Y T C I C P E G Y S G L F C E F S P    H-slit1

1104 M I S M M Y P Q T S P C Q N H E C K H G V - C F Q P N A Q G S D Y L C R C H P G    D-Slit
1112 - - P M V L P R T S P C D N F D C Q N G A Q C I - - - V R I N E P I C Q C L P G    H-slit1

1143 Y T G K W C E Y L T S I S F V H N N S F V E L E P L R T R P E A N V T I V F S S    D-Slit
1147 Y Q G E K C E K L V S V N F I N K E S Y L Q I P S A K V R P Q T N I T L Q I A T    H-slit1

1183 A E Q N G I L M Y D G Q D A H L A V E L F N G R I R V S Y D V G N H P V S T M Y    D-Slit
1187 D E D S G I L L Y K G D K D H I A V E L Y R G R V R A S Y D T G S H P A S A I Y    H-slit1

1223 S F E M V A D G K Y H A V E L L A I K K N F T L R V D R G L A R S I N E G S N    D-Slit
1227 S V E T I N D G N F H I V E L L A L D Q S L S L S V D G G N P K I I T N L S K Q    H-slit1

1263 D Y L K L T T P M F L G G L P V D P A Q Q A Y K N W Q I R N L T S F K G C M K E    D-Slit
1267 S T L N F D S P L Y V G G M P G K S N V A S L R Q A P G Q N G T S F H G C I R N    H-slit1

1303 V W I N H K L V D F G N A Q R Q Q K I T P G C A L - - - - L E G E Q Q E E E D D    D-Slit
1307 L Y I N S E L Q D F Q K V P M Q T G I L P G C E P C H K K V C A H G T C Q P S S    H-slit1

1339 E Q D F M D E - - - - - - T P H I K E E P V D P C L E N K C R R G S R C V P N S    D-Slit
1347 Q A G F T C E C Q E G W M G P L C D Q R T N D P C L G N K C V H G T - C L P I N    H-slit1

1373 N A R D G Y Q C K C K H G Q R G R Y C D Q G E G S T E P - - - - - - - - - - - -    D-Slit
1386 A F - - S Y S C K C L E G H G G V L C D E E E D L F N P C Q A I K C K H G K C R    H-slit1

1401 - - - - - - - - - - - P T V T A A S - - - - - T C R K E Q V R E Y Y T E N D -    D-Slit
1424 L S G L G Q P Y C E C S S G Y T G D S C D R E I S C R G E R I R D Y Y Q K Q Q G    H-slit1

1423 - - - C R S R Q P L K Y A K C V G G C - G N Q C C A A K I V R R R K V R M V C S    D-Slit
1464 Y A A C Q T T K K V S R L E C R G G C A G G Q C C G P L R S K R R K Y S F E C T    H-slit1

1459 N N R K Y I K N L D I V R K C G C T K K C Y                                        D-Slit
1504 D G S S F V D E V E K V V K C G C T R - C V S                                      H-slit1
```

Exemplary such human Slit-1 immunogenic and/or antigenic peptides are shown in Table 3.

TABLE 3

Immunogenic human Slit-1 polypeptides eliciting Slit-1 specific rabbit polyclonal antibody: Slit polypeptide-KLH conjugates immunized per protocol described above.

| Slit Polypeptide | Immunogenicity |
| --- | --- |
| SEQ ID NO:02, res. 1–10 | +++ |
| SEQ ID NO:02, res. 29–41 | +++ |
| SEQ ID NO:02, res. 75–87 | +++ |
| SEQ ID NO:02, res. 92–109 | +++ |
| SEQ ID NO:02, res. 132–141 | +++ |
| SEQ ID NO:02, res. 192–205 | +++ |
| SEQ ID NO:02, res. 258–269 | +++ |
| SEQ ID NO:02, res. 295–311 | +++ |
| SEQ ID NO:02, res. 316–330 | +++ |
| SEQ ID NO:02, res. 373–382 | +++ |
| SEQ ID NO:02, res. 403–422 | +++ |
| SEQ ID NO:02, res. 474–485 | +++ |
| SEQ ID NO:02, res. 561–576 | +++ |
| SEQ ID NO:02, res. 683–697 | +++ |
| SEQ ID NO:02, res. 768–777 | +++ |
| SEQ ID NO:02, res. 798–813 | +++ |
| SEQ ID NO:02, res. 882–894 | +++ |
| SEQ ID NO:02, res. 934–946 | +++ |
| SEQ ID NO:02, res. 1054–1067 | +++ |
| SEQ ID NO:02, res. 1181–1192 | +++ |
| SEQ ID NO:02, res. 1273–1299 | +++ |
| SEQ ID NO:02, res. 1383–1397 | +++ |
| SEQ ID NO:02, res. 1468–1477 | +++ |
| SEQ ID NO:02, res. 1508–1517 | +++ |

The subject domains provide Slit domain specific activity or function, such as Slit-specific cell, especially neuron modulating or modulating inhibitory activity, Slit-ligand-binding or binding inhibitory activity. Slit-specific activity or function may be determined by convenient in vitro, cell-based, or in vivo assays: e.g. in vitro binding assays, cell culture assays, in animals (e.g. gene therapy, transgenics, etc.), etc. The binding target may be a natural intracellular binding target, a Slit regulating protein or other regulator that directly modulates Slit activity or its localization; or non-natural binding target such as a specific immune protein such as an antibody, or a Slit specific agent such as those identified in screening assays such as described below. Slit-binding specificity may be assayed by binding equilibrium constants (usually at least about $10^7$ M$^{-1}$, preferably at least about $10^8$ M$^{-1}$, more preferably at least about $10^9$ M$^{-1}$), by the ability of the subject polypeptide to function as negative mutants in Slit-expressing cells, to elicit Slit specific antibody in a heterologous host (e.g a rodent or rabbit), etc.

In one embodiment, the Slit polypeptides are encoded by a nucleic acid comprising SEQ ID NO:01 or a fragment thereof which hybridizes with a full-length strand thereof, preferably under stringent conditions. Such nucleic acids comprise at least 36, preferably at least 72, more preferably at least 144 and most preferably at least 288 nucleotides of SEQ ID NO:01. Demonstrating specific hybridization generally requires stringent conditions, for example, hybridizing in a buffer comprising 30% formamide in 5×SSPE (0.18 M NaCl, 0.01 M NaPO$_4$, pH 7.7, 0.001 M EDTA) buffer at a temperature of 42° C. and remaining bound when subject to washing at 42° C. with 0.2×SSPE (Conditions I); preferably hybridizing in a buffer comprising 50% formamide in 5×SSPE buffer at a temperature of 42° C. and remaining bound when subject to washing at 42° C. with 0.2×SSPE buffer at 42° C. (Conditions II). Exemplary nucleic acids which hybridize with a strand of SEQ ID NO:01 are shown in Table 4.

TABLE 4

Exemplary nucleic acids which hybridize with a strand of SEQ ID NO:01 under Conditions I and/or II.

| Slit Nucleic Acid | Hybridization |
| --- | --- |
| SEQ ID NO:01, nucl. 1–47 | + |
| SEQ ID NO:01, nucl. 58–99 | + |
| SEQ ID NO:01, nucl. 95–138 | + |
| SEQ ID NO:01, nucl. 181–220 | + |
| SEQ ID NO:01, nucl. 261–299 | + |
| SEQ ID NO:01, nucl. 274–315 | + |
| SEQ ID NO:01, nucl. 351–389 | + |
| SEQ ID NO:01, nucl. 450–593 | + |
| SEQ ID NO:01, nucl. 524–546 | + |
| SEQ ID NO:01, nucl. 561–608 | + |
| SEQ ID NO:01, nucl. 689–727 | + |
| SEQ ID NO:01, nucl. 708–737 | + |
| SEQ ID NO:01, nucl. 738–801 | + |
| SEQ ID NO:01, nucl. 805–854 | + |
| SEQ ID NO:01, nucl. 855–907 | + |
| SEQ ID NO:01, nucl. 910–953 | + |
| SEQ ID NO:01, nucl. 1007–1059 | + |
| SEQ ID NO:01, nucl. 1147–1163 | + |
| SEQ ID NO:01, nucl. 1258–1279 | + |
| SEQ ID NO:01, nucl. 1375–1389 | + |
| SEQ ID NO:01, nucl. 1581–1595 | + |
| SEQ ID NO:01, nucl. 1621–1639 | + |
| SEQ ID NO:01, nucl. 1744–1755 | + |
| SEQ ID NO:01, nucl. 1951–1969 | + |
| SEQ ID NO:01, nucl. 2150–2163 | + |
| SEQ ID NO:01, nucl. 2524–2546 | + |
| SEQ ID NO:01, nucl. 2761–2780 | + |
| SEQ ID NO:01, nucl. 2989–2999 | + |
| SEQ ID NO:01, nucl. 3108–3117 | + |
| SEQ ID NO:01, nucl. 3338–3351 | + |
| SEQ ID NO:01, nucl. 3505–3514 | + |
| SEQ ID NO:01, nucl. 3855–3867 | + |
| SEQ ID NO:01, nucl. 4010–4025 | + |
| SEQ ID NO:01, nucl. 4207–4219 | + |
| SEQ ID NO:01, nucl. 4333–4345 | + |
| SEQ ID NO:01, nucl. 4521–4529 | + |

A wide variety of cell types express Robo polypeptides subject to regulation by the disclosed methods, including many neuronal cells, transformed cells, infected (e.g. virus) cells, etc. Ascertaining Robo binding or activation is readily effected by binding assays or cells function assays as disclosed herein or in the cited copending applications. Accordingly, indications for the subject methods encompass a wide variety of cell types and function, including axon outgrowth, tumor cell invasion or migration, etc. The target cell may reside in culture or in situ, i.e. within the natural host. For in situ applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Slit polypeptides may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic polypeptides. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts.

In one embodiment, the invention provides administering the subject Slit polypeptides in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations for polypeptide-based therapeutics are known in the art. The compositions may be provided in any convenient form including tablets, capsules, troches, powders, sprays, creams, etc. As such the compositions, in pharmaceutically acceptable dosage units or in bulk, may be incorporated into a wide variety of containers. For example, dosage units may be included in a variety of containers including capsules, pills, etc. The compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics*, 9$^{th}$ Ed., 1996, McGraw-Hill.

In another aspect, the invention provides methods of screening for agents which modulate Robo-Slit interactions. These methods generally involve forming a mixture of a Robo-expressing cell, a Slit polypeptide and a candidate agent, and determining the effect of the agent on the amount of Robo expressed by the cell. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Cell and animal based neural guidance/repulsion assays are described in detail in the experimental section below.

The amino acid sequences of the disclosed vertebrate Slit polypeptides are used to back-translate Slit polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural Slit-encoding nucleic acid sequences ("GCG" software, Genetics Computer Group, Inc, Madison Wis.). Slit-encoding nucleic acids used in Slit-expression vectors and incorporated into recombinant host cells, e.g. for expression and screening, transgenic animals, e.g. for functional studies such as the efficacy of candidate drugs for disease associated with Slit-modulated cell function, etc.

The invention also provides nucleic acid hybridization probes and replication/amplification primers having a vertebrate Slit cDNA specific sequence comprising a fragment of a disclosed vertebrate cDNA sequence, and sufficient to effect specific hybridization thereto. Such primers or probes are at least 12, preferably at least 24, more preferably at least 36 and most preferably at least 96 nucleotides in length. Demonstrating specific hybridization generally requires stringent conditions, for example, hybridizing in a buffer comprising 30% formamide in 5×SSPE (0.18 M NaCl, 0.01 M NaPO$_4$, pH 7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Slit nucleic acids can also be distinguished using alignment algorithms, such as BLASTX (Altschul et al. (1990) Basic Local Alignment Search Tool, J Mol Biol 215, 403–410). In addition, the invention provides nucleic acids having a sequence about 60–70%, preferably about 70–80%, more preferably about 80–90%, more preferably about 90–95%, most preferably about 95–99% similar to a vertebrate Slit sequence disclosed herein as determined by Best Fit analysis using default settings and is other than a natural *drosophila* Slit sequence, preferably other than a natural invertebrate Slit sequence. In a particular embodiment, the Slit polynucleotide fragments comprise species specific fragments; such fragments are readily discerned from alignments of the disclosed sequences.

The subject nucleic acids are of synthetic/non-natural sequences and/or are recombinant, meaning they comprise a non-natural sequence or a natural sequence joined to nucleotide(s) other than that which it is joined to on a natural chromosome. The subject recombinant nucleic acids comprising the nucleotide sequence of disclosed vertebrate Slit nucleic acids, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bp, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of Slit genes and gene transcripts and in detecting or amplifying nucleic acids encoding additional Slit homologs and structural analogs. In diagnosis, Slit hybridization probes find use in identifying wild-type and mutant Slit alleles in clinical and laboratory samples. Mutant alleles are used to generate allele-specific oligonucleotide (ASO) probes for high-throughput clinical diagnoses. In therapy, therapeutic Slit nucleic acids are used to modulate cellular expression or intracellular concentration or availability of active Slit. Exemplary human Slit-1 probes and primers are shown in Table 5 and Table 6.

TABLE 5

Hybridization Probes for Regions of Human Slit-1.

| | |
|---|---|
| Hybridization probe for first leucine rich repeat region | SEQ ID NO:01, nucleotides 82–828 |
| Hybridization probe for second leucine rich repeat region | SEQ ID NO:01, nucleotides 829–1503 |
| Hybridization probe for third leucine rich repeat region | SEQ ID NO:01, nucleotides 1504–2166 |
| Hybridization probe for fourth leucine rich repeat region | SEQ ID NO:01, nucleotides 2167–2751 |
| Hybridization probe for EGF repeats one to five | SEQ ID NO:01, nucleotides 2752–3327 |
| Hybridization probe for the sixth EGF repeat and preceding spacer region | SEQ ID NO:01, nucleotides 3328–3461 |
| Hybridization probe for the 99aa spacer/G-loop region | SEQ ID NO:01, nucleotides 3462–3987 |
| Hybridization probe for EGF repeats seven to nine | SEQ ID NO:01, nucleotides 3988–4341 |
| Hybridization probe for the cysteine knot region | SEQ ID NO:01, nucleotides 4342–4575 |

TABLE 6

PCR Primers for regions of Human Slit.

| | |
|---|---|
| PCR Primers for first leucine rich repeat region | Forward: SEQ ID NO:01, nucleotides 82–111<br>Reverse: reverse complement of SEQ ID NO:01, nucleotides 799–828 |
| PCR Primers for second leucine rich repeat region | Forward: SEQ ID NO:01, nucleotides 829–858<br>Reverse: reverse complement of SEQ ID NO:01, nucleotides 1474–1503 |
| PCR Primers for third leucine rich repeat region | Forward: SEQ ID NO:01, nucleotides 1504–1533<br>Reverse: reverse complement of SEQ ID NO:01, nucleotides 2137–2166 |
| PCR Primers for fourth leucine rich repeat region | Forward: SEQ ID NO:01, nucleotides 2167–2196<br>Reverse: reverse complement of SEQ ID NO:01, nucleotides 2722–2751 |
| PCR Primers for EGF repeats one to five | Forward: SEQ ID NO:01, nucleotides 2752–2781<br>Reverse: reverse complement of SEQ ID NO:01, nucleotides 3298–3327 |
| PCR Primers for the sixth EGF repeat and preceding spacer region | Forward: SEQ ID NO:01, nucleotides 3328–3357<br>Reverse: reverse complement of SEQ ID NO:01, nucleotides 3432–3461 |
| PCR Primers for the 99aa spacer/G-loop region | Forward: SEQ I:01, nucleotides 3462–3491<br>Reverse: reverse complement of SEQ ID NO:01, nucleotides 3958–3987 |
| PCR Primers for EGF repeats seven to nine | Forward: SEQ ID NO:01, nucleotides 3988–4017<br>Reverse: reverse complement of SEQ ID NO:01, nucleotides 4312–4341 |
| PCR Primers for the cysteine knot region | Forward: SEQ ID NO:01, nucleotides 4342–4371<br>Reverse: reverse complement of SEQ ID NO:01, nucleotides 4546–4575 |

Leucine rich repeats (LRRs) are predicted by comparison with known proteins and by the presence of a leucine rich core sequence. In slit proteins, the LRRs are flanked by conserved sequences referred to as the amino- and carboxy-flanking regions. These flanking regions are found in other known proteins, but only in a few instances are both the amino- and carboxy-flank regions present in a single protein. The so called "99aa spacer" is actually ~200 amino acids in the *Drosophila* protein and 174 amino acids in Human Slit-1. This region shows homology to the G-loops of laminin A chains.

Cysteine knots are dimerisation domains defined by the presence of six cysteine residues between which disulphide bridges form. The only absolutely conserved residues are the six cysteines, and spacing between them is highly variable, apart from between cysteines 2 and 3, and 5 and 6. The glycine between cysteines 2 and 3 is only present in a subset of cysteine knots. *Drosophila* slit and Human slit-1 both have an extra cysteine after cysteines 5 and 6: this may serve as an intermolecular bond. Human Slit-1 gene displays the overall structure of the *Drosophila* gene, and amino acid conservation is found along the entire length of the protein (48% homology at the amino acid sequence excluding the signal sequence; see below). The Human gene has an extra LRR between LRR2 and LRR3 of the first set of LRRs; in the third set, the Human gene has an extra LRR between LRR3 and LRR4. The Human gene has two extra EGF repeats, on either side of the seventh EGF repeat in *Drosophila* slit.

Isolation of Human Slit-1

Searching of the EST database revealed an EST, ab16g10.r1, with homology to the 99aa spacer region of *Drosophila* slit. This EST was used to probe a Human fetal brain library (Stratagene), and clones for Human slit-1 were isolated.

Features of Human Slit Predicted Protein

| | |
|---|---|
| Signal sequence | SEQ ID NO:02, residues 7–24 |
| First amino-flanking sequence | SEQ ID NO:02, residues 28–59 |
| First set of Leucine Rich Repeats | SEQ ID NO:02, residues 60–179 (6 repeats) |
| First carboxy-flanking sequence | SEQ ID NO:02, residues 180–276 |
| Second amino-flanking sequence | SEQ ID NO:02, residues 277–308 |
| Second set of Leucine Rich Repeats | SEQ ID NO:02, residues 309–434 (5 repeats) |
| Second carboxy-flanking sequence | SEQ ID NO:02, residues 435–501 |
| Third amino-flanking sequence | SEQ ID NO:02, residues 502–533 |
| Third set of Leucine Rich Repeats | SEQ ID NO:02, residues 534–560 (5 repeats) |
| Third carboxy-flanking sequence | SEQ ID NO:02, residues 661–722 |
| Fourth amino-flanking sequence | SEQ ID NO:02, residues 723–754 |
| Fourth set of Leucine Rich Repeats | SEQ ID NO:02, residues 755–855 (4 repeats) |
| Fourth carboxy-flanking sequence | SEQ ID NO:02, residues 856–917 |
| First EGF repeat | SEQ ID NO:02, residues 918–952 |
| Second EGF repeat | SEQ ID NO:02, residues 953–993 |
| Third EGF repeat | SEQ ID NO:02, residues 994–1031 |
| Fourth EGF repeat | SEQ ID NO:02, residues 1032–1071 |
| Fifth EGF repeat | SEQ ID NO:02, residues 1072–1109 |
| Spacer | SEQ ID NO:02, residues 1110–1116 |
| Sixth EGF repeat | SEQ ID NO:02, residues 1117–1153 |
| "99aa spacer" | SEQ ID NO:02, residues 1155–1329 |
| Seventh EGF repeat | SEQ ID NO:02, residues 1330–1366 |
| Eighth EGF repeat | SEQ ID NO:02, residues 1367–1404 |
| Ninth EGF repeat | SEQ ID NO:02, residues 1405–1447 |
| Cysteine knot motif | SEQ ID NO:02, residues 1448–1525 |

Amino Acid Identity Between *Drosophila* and Human Slit-1

| | |
|---|---|
| First amino-flanking sequence | 53% |
| First set of Leucine Rich Repeats | 52% (54%, 67%, NA, 38%, 54%, 50%) |
| First carboxy-flanking sequence | 42% |

-continued

| | |
|---|---|
| Second amino-flanking sequence | 50% |
| Second set of Leucine Rich Repeats | 60% (54%, 58%, 67%, 71%, 50%) |
| Second carboxy-flanking sequence | 62% |
| Third amino-flanking sequence | 56% |
| Third set of Leucine Rich Repeats | 49% (46%, 46%, 42%, NA, 58%) |
| Third carboxy-flanking sequence | 36% |
| Fourth amino-flanking sequence | 53% |
| Fourth set of Leucine Rich Repeats | 48% (25%, 58%, 46%, 63%) |
| Fourth carboxy-flanking sequence | 63% |
| First EGF repeat | 34% |
| Second EGF repeat | 46% |
| Third EGF repeat | 46% |
| Fourth EGF repeat | 35% |
| Fifth EGF repeat | 47% |
| Spacer | 22% |
| Sixth EGF repeat | 40% |
| "99aa spacer" | 38% |
| Seventh EGF repeat | 11%/NA |
| Eighth EGF repeat | 44% |
| Nineth EGF repeat | 29%/NA |
| Cysteine knot motif | 34% |

NA: not applicable due to absence of homologous repeat.

Figures for Individual LLRs are Shown in Brackets.

The following examplary assay is offered by way of illustration and not by way of limitation:

EXAMPLES

Protocol for Ligand Screening of Transfected COS Cells

I. Prepare the Ligand

Expression Construct: cDNAs encoding targeted Slit polypeptides are tagged with the Fc portion of human IgG and subcloned into a 293 expression vector (pCEP4: In Vitrogen).

Transfection: 293 EBNA cells are transfected (CaPO$_4$ method) with the Slit expression constructs. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Prepare Truncated Receptor (Positive Control)

Expression Construct: cDNA encoding a corresponding Robo C-terminal deletion mutant comprising the extracellular domain (truncated immediately N-terminal to the transmembrane region) is subcloned into a 293 expression vector (pCEP4: In Vitrogen).

Transfection: 293 EBNA cells are transfected (CaPO$_4$ method) with the receptor mutant expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Transfect COS Cells

Seed COS cells (250,000) on 35 mm dishes in 2 ml DME/10% FCS.

18–24 h later, dilute 1 ug of Robo-encoding DNA (cDNA cloned into pMT21 expression vector) into 200 ul serum-free media and add 6 ul of Lipofectamine (Gibco). Incubate this solution at room temperature for 15–45 min.

Wash the cells 2× with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

III. Ligand Binding Assay

Wash plates of transfected COS cells 1× with cold PBS (plus Ca/Mg)/1% goat serum. Add 1 ml conditioned media neat and incubate 90 min at room temp.

Wash plates 3× with PBS (plus Ca/Mg). On the 4th wash, add 1 ml 50% methanol to 1 ml PBS. Then add 1 ml methanol. Evacuate and add 1 ml methanol.

Wash 1× with PBS. Wash 1× PBS/1% goat serum.

Add secondary antibody (1-to-2,000 anti-human Fc conjugated to alkaline phosphatase (Jackson Lab)) in PBS/1% goat serum. Incubate 30–40 min room temp.

Wash 3× with PBS. Wash 1× alkaline phosphatase buffer (100 mM Tris-Cl, pH 9.5, 100 mM NaCl, 5 mM $MgCl_2$). Prepare alkaline phosphatase reagents: 4.5 ul/ml NBT and 3.5 ul/ml BCIP (Gibco) in alkaline phosphatase buffer.

Incubate 10–30 min, quench with 20 mM EDTA in PBS. Cells that have bound Slit polypeptides are visible by the presence of a dark purple reaction product.

In parallel incubations, positive controls are provided by titrating Slit binding with serial dilutions of the mutant receptor conditioned medium.

IV. Results: Binding of Slit to Robo

Cell expressing mammalian Slit polypeptides were shown to bind Robo. No reactivity was observed with control COS cells or with receptor-expressing COS cells in the presence of the secondary antibody but in the absence of the Slit-Fc fusion. Binding was observed to receptor-expression cells using a construct in which a Slit polypeptide is fused directly to alkaline phosphatase, for which a secondary antibody is not required. Receptor deletion mutants titrate the Slit-Robo binding, serving as a positive control for inhibition assays.

Protocol for High Throughput Robo-Slit Binding Assay

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P Robo polypeptide 10× stock: $10^{-8}$–$10^{-6}$ M "cold" Robo polypeptide specific Robo domain supplemented with 200,000–250,000 cpm of labeled Robo (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

Slit: $10^{-7}$–$10^{-5}$ M biotinylated Slit in PBS.

B. Preparation of Assay Plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-Robo (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 μM biotinylated Slit (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for All Assays (Located on Each Plate):

a. Non-specific binding b. Soluble (non-biotinylated Slit) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated antibody that specifically binds a slit protein comprising the sequence of SEQ. ID NO:2.

2. The antibody of claim 1 which is a polyclonal antibody.

3. The antibody of claim 1 which is a monoclonal antibody.

4. The antibody of claim 1, wherein the antibody is produced using an immunogenic fragment of SEQ. ID NO:2.

5. The antibody of claim 4, wherein the immunogenic fragment of SEQ ID NO:2 is selected from the group consisting of residues 1–10, 29–41, 75–87, 92–109, 132–141, 192–205, 258–269, 295–311, 316–330, 373–382, 403–422, 474–485, 561–576, 683–697, 768–777, 798–813, 882–894, 934–946, 1054–1067, 1181–1192, 1273–1299, 1383–1397, 1468–1477, 1508–1517, of SEQ ID NO:2.

6. A composition comprising an antibody that specifically binds a slit protein comprising the sequence of SEQ ID NO:2.

7. The composition of claim 6, wherein the antibody is a polyclonal antibody.

8. The composition of claim 6, wherein the antibody is a monoclonal antibody.

9. The composition of claim 6, wherein the antibody is produced using an immunogenic fragment of SEQ ID NO:2.

10. The composition of claim 6, wherein the immunogenic fragment of SEQ ID NO:2 is selected from the group consisting of residues 1–10, 29–41, 75–87, 92–109, 132–141, 192–205, 258–269, 295–311, 316–330, 373–382, 403–422, 474–485, 561–576, 683–697, 768–777, 798–813, 882–894, 934–946, 1054–1067, 1181–1192, 1273–1299, 1383–1397, 1468–1477, 1508–1517, of SEQ ID NO:2.

11. The composition of claim 6, further comprising a pharmaceutically acceptable excipient.

12. An isolated antibody that specifically binds a Slit polypeptide comprising SEQ ID NO:2, or a subsequence thereof having at least 16 consecutive amino acids residues thereof and comprising one or more unboxed amino acid residues of SEQ ID NO:2 in at least one table selected from the group consisting of Table 1 and Table 2.

13. An isolated antibody that specifically binds a Slit polypeptide according to claim 12, wherein the Slit polypeptide comprises SEQ ID NO:2, or a subsequence thereof having at least 64 consecutive amino acid residues thereof and comprising one or more unboxed amino acid residues of the corresponding sequence in at least one table selected from the group consisting of Table 1 and Table 2.

14. An isolated antibody that specifically binds a Slit polypeptide consisting of SEQ ID NO:2.

15. An isolated antibody that specifically binds a Slit polypeptide according to claim 12, wherein the Slit polypeptide comprises SEQ ID NO:2, or a subsequence thereof having at least 16 consecutive amino acid residues thereof and comprising one or more unboxed amino acid residues of the corresponding sequence in Table 2.

16. An isolated antibody that specifically binds a Slit polypeptide according to claim 12, wherein the Slit polypeptide comprises SEQ ID NO:2, or a subsequence thereof having at least 64 consecutive amino acid residues thereof and comprising one or more unboxed amino acid residues of the corresponding sequence in Table 2.

17. The antibody of claim 12, wherein the antibody is produced using an immunogenic fragment of SEQ ID NO:2.

18. The antibody of claim 17, wherein the immunogenic fragment of SEQ ID NO:2 is selected from the group of residues 1–10, 29–41, 75–87, 92–109, 132–141, 192–205, 258–269, 295–311, 316–330, 373–382, 403–422, 474–485, 561–576, 683–697, 768–777, 798–813, 882–894, 934–946, 1054–1067, 1181–1192, 1273–1299, 1383–1397, 1468–1477, and 1508–1517 of SEQ ID NO:2.

19. An isolated antibody that specifically binds a fragment of Slit polypeptide SEQ ID NO:2 having one or more Slit domain selected from the group of a leucine rich repeat, an EGF repeat and cysteine knot motif.

20. The antibody of claim 19, wherein the leucine rich repeat is selected from the group of one or more of residues 60–179, 309–434, 534–560, and 755–855 of SEQ ID NO:2.

21. The antibody of claim 19, wherein the EGF repeat is selected from the group of one or more of residues 918–952, 953–993, 994–1031, 1032–1071, 1072–1109, 1117–1153, 1330–1366, 1367–1404, and 1405–1447 of SEQ ID NO:2.

22. The antibody of claim 19, wherein the cysteine knot motif is residues 1448–1525 of SEQ ID NO:2.

23. The antibody of claim 19, wherein the antibody is produced using a leucine rich repeat or EGF repeat fragment of SEQ ID NO:2.

24. The antibody of claim 23, wherein the leucine rich repeat of SEQ ID NO:2 is selected from the group of residues 60–179, 309–434, 534–560, and 755–855 of SEQ ID NO:2.

25. The antibody of claim 23, wherein the EGF repeat of SEQ ID NO:2 is selected from the group of residues 918–952, 953–993, 994–1031, 1032–1071, 1072–1109, 1117–1153, 1330–1366, 1367–1404, and 1405–1447 of SEQ ID NO:2.

26. The antibody of any of claims 12–25 which is a polyclonal antibody.

27. The antibody of any of claims 12–25 which is a monoclonal antibody.

28. A composition comprising an antibody that specifically binds a Slit polypeptide comprising the sequence of SEQ ID NO:2, or a subsequence thereof having at least 16 consecutive amino acid residues thereof and comprising one or more unboxed amino acid residues of SEQ ID NO:2 in at least one table selected from the group consisting of Table 1 and Table 2, further comprising a pharmaceutically acceptable excipient.

29. The composition of claim 28, wherein the antibody is polyclonal antibody.

30. The composition of claim 28, wherein the antibody is a monoclonal antibody.

31. A method of screening for an antibody that modulates Robo/Slit interaction comprising:

(a) forming a mixture of a Robo-expressing cell, a Slit polypeptide comprising the sequence of SEQ ID NO:2, and a candidate antibody; and (b) determining the effect of the antibody on the amount of Robo expressed by the cell or on the activity of the Robo expressed by the cell, wherein a change in the amount of Robo expressed by the cell or in the activity of the Robo expressed by the cell in the presence of the candidate antibody indicates that the antibody modulates Robo/Slit interaction.

* * * * *

SEQUENCE LISTING

<160> NUMBER OF SEQ ID NOS: 20

<210> SEQ ID NO 1
<211> LENGTH: 4758
<212> TYPE: DNA
<213> ORGANISM: human
<220> FEATURE:
<221> NAME/KEY: CDS
<222> LOCATION: (1)..(4575)

<400> SEQUENCE: 1

-continued

```
atg cgc ggc gtt ggc tgg cag atg ctg tcc ctg tcg ctg ggg tta gtg        48
Met Arg Gly Val Gly Trp Gln Met Leu Ser Leu Ser Leu Gly Leu Val
 1               5                  10                  15 ctg gcg atc ctg aac aag gtg gca ccg cag gcg tgc ccg gcg cag tgc        96
Leu Ala Ile Leu Asn Lys Val Ala Pro Gln Ala Cys Pro Ala Gln Cys
             20                  25                  30 tct tgc tcg ggc agc aca gtg gac tgt cac ggg ctg gcg ctg cgc agc       144
Ser Cys Ser Gly Ser Thr Val Asp Cys His Gly Leu Ala Leu Arg Ser
         35                  40                  45 gtg ccc agg aat atc ccc cgc aac acc gag aga ctg gat tta aat gga       192
Val Pro Arg Asn Ile Pro Arg Asn Thr Glu Arg Leu Asp Leu Asn Gly
     50                  55                  60 aat aac atc aca aga att acg aag aca gat ttt gct ggt ctt aga cat       240
Asn Asn Ile Thr Arg Ile Thr Lys Thr Asp Phe Ala Gly Leu Arg His
 65                  70                  75                  80 cta aga gtt ctt cag ctt atg gag aat aag att agc acc att gaa aga       288
Leu Arg Val Leu Gln Leu Met Glu Asn Lys Ile Ser Thr Ile Glu Arg
                 85                  90                  95 gga gca ttc cag gat ctt aaa gaa cta gag aga ctg cgt tta aac aga       336
Gly Ala Phe Gln Asp Leu Lys Glu Leu Glu Arg Leu Arg Leu Asn Arg
             100                 105                 110 aat cac ctt cag ctg ttt cct gag ttg ctg ttt ctt ggg act gcg aag       384
Asn His Leu Gln Leu Phe Pro Glu Leu Leu Phe Leu Gly Thr Ala Lys
         115                 120                 125 cta tac agg ctt gat ctc agt gaa aac caa att cag gca atc cca agg       432
Leu Tyr Arg Leu Asp Leu Ser Glu Asn Gln Ile Gln Ala Ile Pro Arg
     130                 135                 140 aaa gct ttc cgt ggg gca gtt gac ata aaa aat ttg caa ctg gat tac       480
Lys Ala Phe Arg Gly Ala Val Asp Ile Lys Asn Leu Gln Leu Asp Tyr
145                 150                 155                 160 aac cag atc agc tgt att gaa gat ggg gca ttc agg gct ctc cgg gac       528
Asn Gln Ile Ser Cys Ile Glu Asp Gly Ala Phe Arg Ala Leu Arg Asp
                 165                 170                 175 ctg gaa gtg ctc act ctc aac aat aac aac att act aga ctt tct gtg       576
Leu Glu Val Leu Thr Leu Asn Asn Asn Asn Ile Thr Arg Leu Ser Val
             180                 185                 190 gca agt ttc aac cat atg cct aaa ctt agg act ttt cga ctg cat tca       624
Ala Ser Phe Asn His Met Pro Lys Leu Arg Thr Phe Arg Leu His Ser
         195                 200                 205 aac aac ctg tat tgt gac tgc cac ctg gcc tgg ctc tcc gac tgg ctt       672
Asn Asn Leu Tyr Cys Asp Cys His Leu Ala Trp Leu Ser Asp Trp Leu
     210                 215                 220 cgc aaa agg cct cgg gtt ggt ctg tac act cag tgt atg ggc ccc tcc       720
Arg Lys Arg Pro Arg Val Gly Leu Tyr Thr Gln Cys Met Gly Pro Ser
225                 230                 235                 240 cac ctg aga ggc cat aat gta gcc gag gtt caa aaa cga gaa ttt gtc       768
His Leu Arg Gly His Asn Val Ala Glu Val Gln Lys Arg Glu Phe Val
                 245                 250                 255 tgc agt gat gag gaa gaa ggt cac cag tca ttt atg gct cct tct tgt       816
Cys Ser Asp Glu Glu Glu Gly His Gln Ser Phe Met Ala Pro Ser Cys
             260                 265                 270 agt gtt ttg cac tgc cct gcc gcc tgt acc tgt agc aac aat atc gta       864
Ser Val Leu His Cys Pro Ala Ala Cys Thr Cys Ser Asn Asn Ile Val
         275                 280                 285 gac tgt cgt ggg aaa ggt ctc act gag atc ccc aca aat ctt cca gag       912
Asp Cys Arg Gly Lys Gly Leu Thr Glu Ile Pro Thr Asn Leu Pro Glu
     290                 295                 300 acc atc aca gaa ata cgt ttg gaa cag aac aca atc aaa gtc atc cct       960
Thr Ile Thr Glu Ile Arg Leu Glu Gln Asn Thr Ile Lys Val Ile Pro
305                 310                 315                 320
```

```
cct gga gct ttc tca cca tat aaa aag ctt aga cga att gac ctg agc      1008
Pro Gly Ala Phe Ser Pro Tyr Lys Lys Leu Arg Arg Ile Asp Leu Ser
                325                 330                 335 aat aat cag atc tct gaa ctt gca cca gat gct ttc caa gga cta cgc      1056
Asn Asn Gln Ile Ser Glu Leu Ala Pro Asp Ala Phe Gln Gly Leu Arg
        340                 345                 350 tct ctg aat tca ctt gtc ctc tat gga aat aaa atc aca gaa ctc ccc      1104
Ser Leu Asn Ser Leu Val Leu Tyr Gly Asn Lys Ile Thr Glu Leu Pro
            355                 360                 365 aaa agt tta ttt gaa gga ctg ttt tcc tta cag ctc cta tta ttg aat      1152
Lys Ser Leu Phe Glu Gly Leu Phe Ser Leu Gln Leu Leu Leu Leu Asn
370                 375                 380 gcc aac aag ata aac tgc ctt cgg gta gat gct ttt cag gat ctc cac      1200
Ala Asn Lys Ile Asn Cys Leu Arg Val Asp Ala Phe Gln Asp Leu His
385                 390                 395                 400 aac ttg aac ctt ctc tcc cta tat gac aac aag ctt cag acc atc gcc      1248
Asn Leu Asn Leu Leu Ser Leu Tyr Asp Asn Lys Leu Gln Thr Ile Ala
                405                 410                 415 aag ggg acc ttt tca cct ctt cgg gcc att caa act atg cat ttg gcc      1296
Lys Gly Thr Phe Ser Pro Leu Arg Ala Ile Gln Thr Met His Leu Ala
            420                 425                 430 cag aac ccc ttt att tgt gac tgc cat ctc aag tgg cta gcg gat tat      1344
Gln Asn Pro Phe Ile Cys Asp Cys His Leu Lys Trp Leu Ala Asp Tyr
        435                 440                 445 ctc cat acc aac ccg att gag acc agt ggt gcc cgt tgc acc agc ccc      1392
Leu His Thr Asn Pro Ile Glu Thr Ser Gly Ala Arg Cys Thr Ser Pro
450                 455                 460 cgc cgc ctg gca aac aaa aga att gga cag atc aaa agc aag aaa ttc      1440
Arg Arg Leu Ala Asn Lys Arg Ile Gly Gln Ile Lys Ser Lys Lys Phe
465                 470                 475                 480 cgt tgt tca ggt aca gaa gat tat cga tca aaa tta agt gga gac tgc      1488
Arg Cys Ser Gly Thr Glu Asp Tyr Arg Ser Lys Leu Ser Gly Asp Cys
                485                 490                 495 ttt gcg gat ctg gct tgc cct gaa aag tgt cgc tgt gaa gga acc aca      1536
Phe Ala Asp Leu Ala Cys Pro Glu Lys Cys Arg Cys Glu Gly Thr Thr
            500                 505                 510 gta gat tgc tct aat caa aag ctc aac aaa atc ccg gag cac att ccc      1584
Val Asp Cys Ser Asn Gln Lys Leu Asn Lys Ile Pro Glu His Ile Pro
        515                 520                 525 cag tac act gca gag ttg cgt ctc aat aat aat gaa ttt acc gtg ttg      1632
Gln Tyr Thr Ala Glu Leu Arg Leu Asn Asn Asn Glu Phe Thr Val Leu
530                 535                 540 gaa gcc aca gga atc ttt aag aaa ctt cct caa tta cgt aaa ata aac      1680
Glu Ala Thr Gly Ile Phe Lys Lys Leu Pro Gln Leu Arg Lys Ile Asn
545                 550                 555                 560 ttt agc aac aat aag atc aca gat att gag gag gga gca ttt gaa gga      1728
Phe Ser Asn Asn Lys Ile Thr Asp Ile Glu Glu Gly Ala Phe Glu Gly
                565                 570                 575 gca tct ggt gta aat gaa ata ctt ctt acg agt aat cgt ttg gaa aat      1776
Ala Ser Gly Val Asn Glu Ile Leu Leu Thr Ser Asn Arg Leu Glu Asn
            580                 585                 590 gtg cag cat aag atg ttc aag gga ttg gaa agc ctc aaa act ttg atg      1824
Val Gln His Lys Met Phe Lys Gly Leu Glu Ser Leu Lys Thr Leu Met
        595                 600                 605 ttg aga agc aat cga ata acc tgt gtg ggg aat gac agt ttc ata gga      1872
Leu Arg Ser Asn Arg Ile Thr Cys Val Gly Asn Asp Ser Phe Ile Gly
610                 615                 620 ctc agt tct gtg cgt ttg ctt tct ttg tat gat aat caa att act aca      1920
Leu Ser Ser Val Arg Leu Leu Ser Leu Tyr Asp Asn Gln Ile Thr Thr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 625 |     |     |     | 630 |     |     |     | 635 |     |     |     | 640 |     |      |
| gtt | gca | cca | ggg | gca | ttt | gat | act | ctc | cat | tct | tta | tct | act | cta | aac | 1968 |
| Val | Ala | Pro | Gly | Ala | Phe | Asp | Thr | Leu | His | Ser | Leu | Ser | Thr | Leu | Asn |      |
|     |     |     |     | 645 |     |     |     |     | 650 |     |     |     |     | 655 |     |      |
| ctc | ttg | gcc | aat | cct | ttt | aac | tgt | aac | tgc | tac | ctg | gct | tgg | ttg | gga | 2016 |
| Leu | Leu | Ala | Asn | Pro | Phe | Asn | Cys | Asn | Cys | Tyr | Leu | Ala | Trp | Leu | Gly |      |
|     |     |     | 660 |     |     |     |     | 665 |     |     |     |     | 670 |     |     |      |
| gag | tgg | ctg | aga | aag | aag | aga | att | gtc | acg | gga | aat | cct | aga | tgt | caa | 2064 |
| Glu | Trp | Leu | Arg | Lys | Lys | Arg | Ile | Val | Thr | Gly | Asn | Pro | Arg | Cys | Gln |      |
|     |     | 675 |     |     |     |     | 680 |     |     |     |     | 685 |     |     |     |      |
| aaa | cca | tac | ttc | ctg | aaa | gaa | ata | ccc | atc | cag | gat | gtg | gcc | att | cag | 2112 |
| Lys | Pro | Tyr | Phe | Leu | Lys | Glu | Ile | Pro | Ile | Gln | Asp | Val | Ala | Ile | Gln |      |
|     | 690 |     |     |     |     | 695 |     |     |     |     | 700 |     |     |     |     |      |
| gac | ttc | act | tgt | gat | gac | gga | aat | gat | gac | aat | agt | tgc | tcc | cca | ctt | 2160 |
| Asp | Phe | Thr | Cys | Asp | Asp | Gly | Asn | Asp | Asp | Asn | Ser | Cys | Ser | Pro | Leu |      |
| 705 |     |     |     |     | 710 |     |     |     |     | 715 |     |     |     |     | 720 |      |
| tct | cgc | tgt | cct | act | gaa | tgt | act | tgc | ttg | gat | aca | gtc | gtc | cga | tgt | 2208 |
| Ser | Arg | Cys | Pro | Thr | Glu | Cys | Thr | Cys | Leu | Asp | Thr | Val | Val | Arg | Cys |      |
|     |     |     |     | 725 |     |     |     |     | 730 |     |     |     |     | 735 |     |      |
| agc | aac | aag | ggt | ttg | aag | gtc | ttg | ccg | aaa | ggt | att | cca | aga | gat | gtc | 2256 |
| Ser | Asn | Lys | Gly | Leu | Lys | Val | Leu | Pro | Lys | Gly | Ile | Pro | Arg | Asp | Val |      |
|     |     |     | 740 |     |     |     |     | 745 |     |     |     |     | 750 |     |     |      |
| aca | gag | ttg | tat | ctg | gat | gga | aac | caa | ttt | aca | ctg | gtt | ccc | aag | gaa | 2304 |
| Thr | Glu | Leu | Tyr | Leu | Asp | Gly | Asn | Gln | Phe | Thr | Leu | Val | Pro | Lys | Glu |      |
|     |     | 755 |     |     |     |     | 760 |     |     |     |     | 765 |     |     |     |      |
| ctc | tcc | aac | tac | aaa | cat | tta | aca | ctt | ata | gac | tta | agt | aac | aac | aga | 2352 |
| Leu | Ser | Asn | Tyr | Lys | His | Leu | Thr | Leu | Ile | Asp | Leu | Ser | Asn | Asn | Arg |      |
|     | 770 |     |     |     |     | 775 |     |     |     |     | 780 |     |     |     |     |      |
| ata | agc | acg | ctt | tct | aat | cag | agc | ttc | agc | aac | atg | acc | cag | ctc | ctc | 2400 |
| Ile | Ser | Thr | Leu | Ser | Asn | Gln | Ser | Phe | Ser | Asn | Met | Thr | Gln | Leu | Leu |      |
| 785 |     |     |     |     | 790 |     |     |     |     | 795 |     |     |     |     | 800 |      |
| acc | tta | att | ctt | agt | tac | aac | cgt | ctg | aga | tgt | att | cct | cct | cgc | acc | 2448 |
| Thr | Leu | Ile | Leu | Ser | Tyr | Asn | Arg | Leu | Arg | Cys | Ile | Pro | Pro | Arg | Thr |      |
|     |     |     |     | 805 |     |     |     |     | 810 |     |     |     |     | 815 |     |      |
| ttt | gat | gga | tta | aag | tct | ctt | cga | tta | ctt | tct | cta | cat | gga | aat | gac | 2496 |
| Phe | Asp | Gly | Leu | Lys | Ser | Leu | Arg | Leu | Leu | Ser | Leu | His | Gly | Asn | Asp |      |
|     |     |     | 820 |     |     |     |     | 825 |     |     |     |     | 830 |     |     |      |
| att | tct | gtt | gtg | cct | gaa | ggt | gct | ttc | aat | gat | ctt | tct | gca | tta | tca | 2544 |
| Ile | Ser | Val | Val | Pro | Glu | Gly | Ala | Phe | Asn | Asp | Leu | Ser | Ala | Leu | Ser |      |
|     |     | 835 |     |     |     |     | 840 |     |     |     |     | 845 |     |     |     |      |
| cat | cta | gca | att | gga | gcc | aac | cct | ctt | tac | tgt | gat | tgt | aac | atg | cag | 2592 |
| His | Leu | Ala | Ile | Gly | Ala | Asn | Pro | Leu | Tyr | Cys | Asp | Cys | Asn | Met | Gln |      |
|     | 850 |     |     |     |     | 855 |     |     |     |     | 860 |     |     |     |     |      |
| tgg | tta | tcc | gac | tgg | gtg | aag | tcg | gaa | tat | aag | gag | cct | gga | att | gct | 2640 |
| Trp | Leu | Ser | Asp | Trp | Val | Lys | Ser | Glu | Tyr | Lys | Glu | Pro | Gly | Ile | Ala |      |
| 865 |     |     |     |     | 870 |     |     |     |     | 875 |     |     |     |     | 880 |      |
| cgt | tgt | gct | ggt | cct | gga | gaa | atg | gca | gat | aaa | ctt | tta | ctc | aca | act | 2688 |
| Arg | Cys | Ala | Gly | Pro | Gly | Glu | Met | Ala | Asp | Lys | Leu | Leu | Leu | Thr | Thr |      |
|     |     |     |     | 885 |     |     |     |     | 890 |     |     |     |     | 895 |     |      |
| ccc | tcc | aaa | aaa | ttt | acc | tgt | caa | ggt | cct | gtg | gat | gtc | aat | att | cta | 2736 |
| Pro | Ser | Lys | Lys | Phe | Thr | Cys | Gln | Gly | Pro | Val | Asp | Val | Asn | Ile | Leu |      |
|     |     |     | 900 |     |     |     |     | 905 |     |     |     |     | 910 |     |     |      |
| gct | aag | tgt | aac | ccc | tgc | cta | tca | aat | ccg | tgt | aaa | aat | gat | ggc | aca | 2784 |
| Ala | Lys | Cys | Asn | Pro | Cys | Leu | Ser | Asn | Pro | Cys | Lys | Asn | Asp | Gly | Thr |      |
|     |     | 915 |     |     |     |     | 920 |     |     |     |     | 925 |     |     |     |      |
| tgt | aat | agt | gat | cca | gtt | gac | ttt | tac | cga | tgc | acc | tgt | cca | tat | ggt | 2832 |
| Cys | Asn | Ser | Asp | Pro | Val | Asp | Phe | Tyr | Arg | Cys | Thr | Cys | Pro | Tyr | Gly |      |
|     | 930 |     |     |     |     | 935 |     |     |     |     | 940 |     |     |     |     |      |
| ttc | aag | ggg | cag | gac | tgt | gat | gtc | cca | att | cat | gcc | tgc | atc | agt | aac | 2880 |

```
                Phe Lys Gly Gln Asp Cys Asp Val Pro Ile His Ala Cys Ile Ser Asn
                945                 950                 955                 960 cca tgt aaa cat gga gga act tgc cac tta aag gaa gga gaa gaa gat          2928
Pro Cys Lys His Gly Gly Thr Cys His Leu Lys Glu Gly Glu Glu Asp
                    965                 970                 975 gga ttc tgg tgt att tgt gct gat gga ttt gaa gga gaa aat tgt gaa          2976
Gly Phe Trp Cys Ile Cys Ala Asp Gly Phe Glu Gly Glu Asn Cys Glu
                980                 985                 990 gtc aac gtt gat gat tgt gaa gat aat gac tgt gaa aat aat tct aca          3024
Val Asn Val Asp Asp Cys Glu Asp Asn Asp Cys Glu Asn Asn Ser Thr
            995                 1000                1005 tgt gtc gat ggc att aat aac tac aca tgc ctt tgc cca cct gag tat          3072
Cys Val Asp Gly Ile Asn Asn Tyr Thr Cys Leu Cys Pro Pro Glu Tyr
        1010                1015                1020 aca ggt gag ttg tgt gag gag aag ctg gac ttc tgt gcc cag gac ctg          3120
Thr Gly Glu Leu Cys Glu Glu Lys Leu Asp Phe Cys Ala Gln Asp Leu
1025                1030                1035                1040 aac ccc tgc cag cac gat tca aag tgc atc cta act cca aag gga ttc          3168
Asn Pro Cys Gln His Asp Ser Lys Cys Ile Leu Thr Pro Lys Gly Phe
                1045                1050                1055 aaa tgt gac tgc aca cca ggg tac gta ggt gaa cac tgc gac atc gat          3216
Lys Cys Asp Cys Thr Pro Gly Tyr Val Gly Glu His Cys Asp Ile Asp
            1060                1065                1070 ttt gac gac tgc caa gac aac aag tgt aaa aac gga gcc cac tgc aca          3264
Phe Asp Asp Cys Gln Asp Asn Lys Cys Lys Asn Gly Ala His Cys Thr
        1075                1080                1085 gat gca gtg aac ggc tat acg tgc ata tgc ccc gaa ggt tac agt ggc          3312
Asp Ala Val Asn Gly Tyr Thr Cys Ile Cys Pro Glu Gly Tyr Ser Gly
    1090                1095                1100 ttg ttc tgt gag ttt tct cca ccc atg gtc ctc cct cgt acc agc ccc          3360
Leu Phe Cys Glu Phe Ser Pro Pro Met Val Leu Pro Arg Thr Ser Pro
1105                1110                1115                1120 tgt gat aat ttt gat tgt cag aat gga gct cag tgt atc gtc aga ata          3408
Cys Asp Asn Phe Asp Cys Gln Asn Gly Ala Gln Cys Ile Val Arg Ile
                1125                1130                1135 aat gag cca ata tgt cag tgt ttg cct ggc tat cag gga gaa aag tgt          3456
Asn Glu Pro Ile Cys Gln Cys Leu Pro Gly Tyr Gln Gly Glu Lys Cys
            1140                1145                1150 gaa aaa ttg gtt agt gtg aat ttt ata aac aaa gag tct tat ctt cag          3504
Glu Lys Leu Val Ser Val Asn Phe Ile Asn Lys Glu Ser Tyr Leu Gln
        1155                1160                1165 att cct tca gcc aag gtt cgg cct cag acg aac ata aca ctt cag att          3552
Ile Pro Ser Ala Lys Val Arg Pro Gln Thr Asn Ile Thr Leu Gln Ile
    1170                1175                1180 gcc aca gat gaa gac agc gga atc ctc ctg tat aag ggt gac aaa gac          3600
Ala Thr Asp Glu Asp Ser Gly Ile Leu Leu Tyr Lys Gly Asp Lys Asp
1185                1190                1195                1200 cat atc gcg gta gaa ctc tat cgg ggg cgt gtt cgt gcc agc tat gac          3648
His Ile Ala Val Glu Leu Tyr Arg Gly Arg Val Arg Ala Ser Tyr Asp
                1205                1210                1215 acc ggc tct cat cca gct tct gcc att tac agt gtg gag aca atc aat          3696
Thr Gly Ser His Pro Ala Ser Ala Ile Tyr Ser Val Glu Thr Ile Asn
            1220                1225                1230 gat gga aac ttc cac att gtg gaa cta ctt gcc ttg gat cag agt ctc          3744
Asp Gly Asn Phe His Ile Val Glu Leu Leu Ala Leu Asp Gln Ser Leu
        1235                1240                1245 tct ttg tcc gtg gat ggt ggg aac ccc aaa atc atc act aac ttg tca          3792
Ser Leu Ser Val Asp Gly Gly Asn Pro Lys Ile Ile Thr Asn Leu Ser
    1250                1255                1260
```

```
aag cag tcc act ctg aat ttt gac tct cca ctc tat gta gga ggc atg      3840
Lys Gln Ser Thr Leu Asn Phe Asp Ser Pro Leu Tyr Val Gly Gly Met
1265                1270                1275                1280 cca ggg aag agt aac gtg gca tct ctg cgc cag gcc cct ggg cag aac      3888
Pro Gly Lys Ser Asn Val Ala Ser Leu Arg Gln Ala Pro Gly Gln Asn
            1285                1290                1295 gga acc agc ttc cac ggc tgc atc cgg aac ctt tac atc aac agt gag      3936
Gly Thr Ser Phe His Gly Cys Ile Arg Asn Leu Tyr Ile Asn Ser Glu
1300                1305                1310 ctg cag gac ttc cag aag gtg ccg atg caa aca ggc att ttg cct ggc      3984
Leu Gln Asp Phe Gln Lys Val Pro Met Gln Thr Gly Ile Leu Pro Gly
        1315                1320                1325 tgt gag cca tgc cac aag aag gtg tgt gcc cat ggc aca tgc cag ccc      4032
Cys Glu Pro Cys His Lys Lys Val Cys Ala His Gly Thr Cys Gln Pro
    1330                1335                1340 agc agc cag gca ggc ttc acc tgc gag tgc cag gaa gga tgg atg ggg      4080
Ser Ser Gln Ala Gly Phe Thr Cys Glu Cys Gln Glu Gly Trp Met Gly
1345                1350                1355                1360 ccc ctc tgt gac caa cgg acc aat gac cct tgc ctt gga aat aaa tgc      4128
Pro Leu Cys Asp Gln Arg Thr Asn Asp Pro Cys Leu Gly Asn Lys Cys
                1365                1370                1375 gta cat ggc acc tgc ttg ccc atc aat gcg ttc tcc tac agc tgt aag      4176
Val His Gly Thr Cys Leu Pro Ile Asn Ala Phe Ser Tyr Ser Cys Lys
            1380                1385                1390 tgc ttg gag ggc cat gga ggt gtc ctc tgt gat gaa gag gag gat ctg      4224
Cys Leu Glu Gly His Gly Gly Val Leu Cys Asp Glu Glu Glu Asp Leu
        1395                1400                1405 ttt aac cca tgc cag gcg atc aag tgc aag cat ggg aag tgc agg ctt      4272
Phe Asn Pro Cys Gln Ala Ile Lys Cys Lys His Gly Lys Cys Arg Leu
    1410                1415                1420 tca ggt ctg ggg cag ccc tac tgt gaa tgc agc agt gga tac acg ggg      4320
Ser Gly Leu Gly Gln Pro Tyr Cys Glu Cys Ser Ser Gly Tyr Thr Gly
1425                1430                1435                1440 gac agc tgt gat cga gaa atc tct tgt cga ggg gaa agg ata aga gat      4368
Asp Ser Cys Asp Arg Glu Ile Ser Cys Arg Gly Glu Arg Ile Arg Asp
                1445                1450                1455 tat tac caa aag cag cag ggc tat gct gct tgc caa aca acc aag aag      4416
Tyr Tyr Gln Lys Gln Gln Gly Tyr Ala Ala Cys Gln Thr Thr Lys Lys
            1460                1465                1470 gtg tcc cga tta gag tgc aga ggt ggg tgt gca gga ggg cag tgc tgt      4464
Val Ser Arg Leu Glu Cys Arg Gly Gly Cys Ala Gly Gly Gln Cys Cys
        1475                1480                1485 gga ccg ctg agg agc aag cgg cgg aaa tac tct ttc gaa tgc act gac      4512
Gly Pro Leu Arg Ser Lys Arg Arg Lys Tyr Ser Phe Glu Cys Thr Asp
    1490                1495                1500 ggc tcc tcc ttt gtg gac gag gtt gag aaa gtg gtg aag tgc ggc tgt      4560
Gly Ser Ser Phe Val Asp Glu Val Glu Lys Val Val Lys Cys Gly Cys
1505                1510                1515                1520 acg agg tgt gtg tcc taaacacact cccggcagct ctgtctttgg aaaaggttgt      4615
Thr Arg Cys Val Ser
            1525 atacttcttg accatgtggg actaatgaat gcttcatagt ggaaatattt gaaatatatt    4675 gtaaaataca gaacagactt attttttatta tgagaataaa gactttttttt ctgcatttgg  4735 aaaaaaaaaa aaaaaaaact cga                                            4758

<210> SEQ ID NO 2
<211> LENGTH: 1525
<212> TYPE: PRT
<213> ORGANISM: human
```

-continued

<400> SEQUENCE: 2

```
Met Arg Gly Val Gly Trp Gln Met Leu Ser Leu Ser Leu Gly Leu Val
 1               5                  10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
 65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Lys Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Thr Ile Lys Val Ile Pro
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
```

-continued

```
                405                 410                 415
Lys Gly Thr Phe Ser Pro Leu Arg Ala Ile Gln Thr Met His Leu Ala
            420                 425                 430
Gln Asn Pro Phe Ile Cys Asp Cys His Leu Lys Trp Leu Ala Asp Tyr
            435                 440                 445
Leu His Thr Asn Pro Ile Glu Thr Ser Gly Ala Arg Cys Thr Ser Pro
            450                 455                 460
Arg Arg Leu Ala Asn Lys Arg Ile Gly Gln Ile Lys Ser Lys Lys Phe
465                 470                 475                 480
Arg Cys Ser Gly Thr Glu Asp Tyr Arg Ser Lys Leu Ser Gly Asp Cys
            485                 490                 495
Phe Ala Asp Leu Ala Cys Pro Glu Lys Cys Arg Cys Glu Gly Thr Thr
            500                 505                 510
Val Asp Cys Ser Asn Gln Lys Leu Asn Lys Ile Pro Glu His Ile Pro
            515                 520                 525
Gln Tyr Thr Ala Glu Leu Arg Leu Asn Asn Asn Glu Phe Thr Val Leu
            530                 535                 540
Glu Ala Thr Gly Ile Phe Lys Lys Leu Pro Gln Leu Arg Lys Ile Asn
545                 550                 555                 560
Phe Ser Asn Asn Lys Ile Thr Asp Ile Glu Glu Gly Ala Phe Glu Gly
                565                 570                 575
Ala Ser Gly Val Asn Glu Ile Leu Leu Thr Ser Asn Arg Leu Glu Asn
            580                 585                 590
Val Gln His Lys Met Phe Lys Gly Leu Glu Ser Leu Lys Thr Leu Met
            595                 600                 605
Leu Arg Ser Asn Arg Ile Thr Cys Val Gly Asn Asp Ser Phe Ile Gly
610                 615                 620
Leu Ser Ser Val Arg Leu Leu Ser Leu Tyr Asp Asn Gln Ile Thr Thr
625                 630                 635                 640
Val Ala Pro Gly Ala Phe Asp Thr Leu His Ser Leu Ser Thr Leu Asn
                645                 650                 655
Leu Leu Ala Asn Pro Phe Asn Cys Asn Cys Tyr Leu Ala Trp Leu Gly
                660                 665                 670
Glu Trp Leu Arg Lys Lys Arg Ile Val Thr Gly Asn Pro Arg Cys Gln
            675                 680                 685
Lys Pro Tyr Phe Leu Lys Glu Ile Pro Ile Gln Asp Val Ala Ile Gln
            690                 695                 700
Asp Phe Thr Cys Asp Asp Gly Asn Asp Asp Asn Ser Cys Ser Pro Leu
705                 710                 715                 720
Ser Arg Cys Pro Thr Glu Cys Thr Cys Leu Asp Thr Val Val Arg Cys
                725                 730                 735
Ser Asn Lys Gly Leu Lys Val Leu Pro Lys Gly Ile Pro Arg Asp Val
            740                 745                 750
Thr Glu Leu Tyr Leu Asp Gly Asn Gln Phe Thr Leu Val Pro Lys Glu
            755                 760                 765
Leu Ser Asn Tyr Lys His Leu Thr Leu Ile Asp Leu Ser Asn Asn Arg
            770                 775                 780
Ile Ser Thr Leu Ser Asn Gln Ser Phe Ser Asn Met Thr Gln Leu Leu
785                 790                 795                 800
Thr Leu Ile Leu Ser Tyr Asn Arg Leu Arg Cys Ile Pro Pro Arg Thr
                805                 810                 815
Phe Asp Gly Leu Lys Ser Leu Arg Leu Leu Ser Leu His Gly Asn Asp
            820                 825                 830
```

```
Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
        850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Val Asn Ile Leu
            900                 905                 910

Ala Lys Cys Asn Pro Cys Leu Ser Asn Pro Cys Lys Asn Asp Gly Thr
        915                 920                 925

Cys Asn Ser Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Glu Asp
                965                 970                 975

Gly Phe Trp Cys Ile Cys Ala Asp Gly Phe Glu Gly Glu Asn Cys Glu
            980                 985                 990

Val Asn Val Asp Asp Cys Glu Asp Asn Asp Cys Glu Asn Asn Ser Thr
        995                 1000                1005

Cys Val Asp Gly Ile Asn Asn Tyr Thr Cys Leu Cys Pro Pro Glu Tyr
    1010                1015                1020

Thr Gly Glu Leu Cys Glu Glu Lys Leu Asp Phe Cys Ala Gln Asp Leu
1025                1030                1035                1040

Asn Pro Cys Gln His Asp Ser Lys Cys Ile Leu Thr Pro Lys Gly Phe
            1045                1050                1055

Lys Cys Asp Cys Thr Pro Gly Tyr Val Gly Glu His Cys Asp Ile Asp
        1060                1065                1070

Phe Asp Asp Cys Gln Asp Asn Lys Cys Lys Asn Gly Ala His Cys Thr
    1075                1080                1085

Asp Ala Val Asn Gly Tyr Thr Cys Ile Cys Pro Glu Gly Tyr Ser Gly
    1090                1095                1100

Leu Phe Cys Glu Phe Ser Pro Pro Met Val Leu Pro Arg Thr Ser Pro
1105                1110                1115                1120

Cys Asp Asn Phe Asp Cys Gln Asn Gly Ala Gln Cys Ile Val Arg Ile
            1125                1130                1135

Asn Glu Pro Ile Cys Gln Cys Leu Pro Gly Tyr Gln Gly Glu Lys Cys
            1140                1145                1150

Glu Lys Leu Val Ser Val Asn Phe Ile Asn Lys Glu Ser Tyr Leu Gln
        1155                1160                1165

Ile Pro Ser Ala Lys Val Arg Pro Gln Thr Asn Ile Thr Leu Gln Ile
        1170                1175                1180

Ala Thr Asp Glu Asp Ser Gly Ile Leu Leu Tyr Lys Gly Asp Lys Asp
1185                1190                1195                1200

His Ile Ala Val Glu Leu Tyr Arg Gly Arg Val Arg Ala Ser Tyr Asp
            1205                1210                1215

Thr Gly Ser His Pro Ala Ser Ala Ile Tyr Ser Val Glu Thr Ile Asn
            1220                1225                1230

Asp Gly Asn Phe His Ile Val Glu Leu Leu Ala Leu Asp Gln Ser Leu
        1235                1240                1245
```

-continued

Ser Leu Ser Val Asp Gly Gly Asn Pro Lys Ile Ile Thr Asn Leu Ser
    1250                1255                1260

Lys Gln Ser Thr Leu Asn Phe Asp Ser Pro Leu Tyr Val Gly Gly Met
1265                1270                1275                1280

Pro Gly Lys Ser Asn Val Ala Ser Leu Arg Gln Ala Pro Gly Gln Asn
            1285                1290                1295

Gly Thr Ser Phe His Gly Cys Ile Arg Asn Leu Tyr Ile Asn Ser Glu
        1300                1305                1310

Leu Gln Asp Phe Gln Lys Val Pro Met Gln Thr Gly Ile Leu Pro Gly
    1315                1320                1325

Cys Glu Pro Cys His Lys Lys Val Cys Ala His Gly Thr Cys Gln Pro
    1330                1335                1340

Ser Ser Gln Ala Gly Phe Thr Cys Glu Cys Gln Glu Gly Trp Met Gly
1345                1350                1355                1360

Pro Leu Cys Asp Gln Arg Thr Asn Asp Pro Cys Leu Gly Asn Lys Cys
            1365                1370                1375

Val His Gly Thr Cys Leu Pro Ile Asn Ala Phe Ser Tyr Ser Cys Lys
        1380                1385                1390

Cys Leu Glu Gly His Gly Gly Val Leu Cys Asp Glu Glu Asp Leu
    1395                1400                1405

Phe Asn Pro Cys Gln Ala Ile Lys Cys Lys His Gly Lys Cys Arg Leu
    1410                1415                1420

Ser Gly Leu Gly Gln Pro Tyr Cys Glu Cys Ser Ser Gly Tyr Thr Gly
1425                1430                1435                1440

Asp Ser Cys Asp Arg Glu Ile Ser Cys Arg Gly Glu Arg Ile Arg Asp
            1445                1450                1455

Tyr Tyr Gln Lys Gln Gly Tyr Ala Ala Cys Gln Thr Thr Lys Lys
        1460                1465                1470

Val Ser Arg Leu Glu Cys Arg Gly Gly Cys Ala Gly Gly Gln Cys Cys
    1475                1480                1485

Gly Pro Leu Arg Ser Lys Arg Arg Lys Tyr Ser Phe Glu Cys Thr Asp
    1490                1495                1500

Gly Ser Ser Phe Val Asp Glu Val Glu Lys Val Val Lys Cys Gly Cys
1505                1510                1515                1520

Thr Arg Cys Val Ser
            1525

<210> SEQ ID NO 3
<211> LENGTH: 105
<212> TYPE: PRT
<213> ORGANISM: human

<400> SEQUENCE: 3

Ser Pro Cys Thr Cys Ser Asn Asn Ile Val Asp Cys Arg Gly Lys Gly
1               5                   10                  15

Leu Met Glu Ile Pro Ala Asn Leu Pro Glu Gly Ile Val Glu Ile Arg
            20                  25                  30

Leu Glu Gln Asn Ser Ile Lys Ala Ile Pro Ala Gly Ala Phe Thr Gln
        35                  40                  45

Tyr Lys Lys Leu Lys Arg Ile Asp Ile Ser Lys Asn Gln Ile Ser Asp
    50                  55                  60

Ile Ala Pro Asp Ala Phe Gln Gly Leu Lys Ser Leu Thr Ser Leu Val
65                  70                  75                  80

Leu Tyr Gly Asn Lys Ile Thr Glu Ile Ala Lys Gly Leu Phe Asp Gly
            85                  90                  95

```
Leu Val Ser Leu Gln Leu Leu Leu Leu
            100                 105

<210> SEQ ID NO 4
<211> LENGTH: 138
<212> TYPE: PRT
<213> ORGANISM: human

<400> SEQUENCE: 4

Glu Gly Ala Phe Asn Gly Ala Ala Ser Val Gln Glu Leu Met Leu Thr
 1               5                  10                  15

Gly Asn Gln Leu Glu Thr Val His Gly Arg Gly Phe Arg Gly Leu
                20                  25                  30      Leu

Ser Gly Leu Lys Thr Leu Met Leu Arg Ser Asn Leu Ile Gly Cys Val
            35                  40                  45

Ser Asn Asp Thr Phe Ala Gly Leu Ser Ser Val Arg Leu Leu Ser Leu
        50                  55                  60

Tyr Asp Asn Arg Ile Thr Thr Ile Thr Pro Gly Ala Phe Thr Thr Leu
 65                  70                  75                  80

Val Ser Leu Ser Thr Ile Asn Leu Leu Ser Asn Pro Phe Asn Cys Asn
                85                  90                  95

Cys His Leu Gly Ala Gly Leu Gly Lys Trp Leu Arg Lys Arg Arg Ile
            100                 105                 110

Val Ser Gly Asn Pro Arg Cys Gln Lys Pro Phe Phe Leu Lys Glu Ile
        115                 120                 125

Pro Ile Gln Gly Val Gly His Pro Gly Ile
        130                 135

<210> SEQ ID NO 5
<211> LENGTH: 160
<212> TYPE: PRT
<213> ORGANISM: human
<220> FEATURE:
<221> NAME/KEY: misc_feature
<222> LOCATION: (121)..(150)
<223> OTHER INFORMATION: note="Xaa signifies gap in sequence"

<400> SEQUENCE: 5

Trp Pro Arg Cys Glu Cys Met Pro Gly Tyr Ala Gly Asp Asn Cys Ser
 1               5                  10                  15

Glu Asn Gln Asp Asp Cys Arg Asp His Arg Cys Gln Asn Gly Ala Gln
                20                  25                  30

Cys Met Asp Glu Val Asn Ser Tyr Ser Cys Leu Cys Ala Glu Gly Tyr
            35                  40                  45

Ser Gly Gln Leu Cys Glu Ile Pro Pro His Leu Pro Ala Pro Lys Ser
        50                  55                  60

Pro Cys Glu Gly Thr Glu Cys Gln Asn Gly Ala Asn Cys Val Asp Gln
 65                  70                  75                  80

Gly Asn Arg Pro Val Cys Gln Cys Leu Pro Gly Phe Gly Gly Pro Glu
                85                  90                  95

Cys Glu Lys Leu Leu Ser Val Asn Phe Val Asp Arg Asp Thr Tyr Leu
            100                 105                 110

Gln Phe Thr Asp Leu Gln Asn Trp Xaa Arg Xaa Asn Ile Thr Leu Gln
        115                 120                 125

Val Phe Thr Ala Glu Asp Asn Gly Ile Leu Leu Tyr Asn Gly Gly Asn
        130                 135                 140

Asp His Ile Ala Val Xaa Leu Tyr Xaa Gly His Val Arg Phe Ser Tyr
```

-continued

```
        145                 150                 155                 160

<210> SEQ ID NO 6
<211> LENGTH: 103
<212> TYPE: PRT
<213> ORGANISM: human

<400> SEQUENCE: 6

Gln Cys His Ile Ser Asp Gln Gly Glu Pro Tyr Cys Leu Cys Gln Pro
  1               5                  10                  15

Gly Phe Ser Gly Glu His Cys Gln Gln Glu Asn Pro Cys Leu Gly Gln
                 20                  25                  30

Val Val Arg Glu Val Ile Arg Arg Gln Lys Gly Tyr Ala Ser Cys Ala
             35                  40                  45

Thr Ala Ser Lys Val Pro Ile Met Glu Cys Arg Gly Gly Cys Gly Pro
         50                  55                  60

Gln Cys Cys Gln Pro Thr Arg Ser Lys Arg Lys Tyr Val Phe Gln
 65                  70                  75                  80

Cys Thr Asp Gly Ser Ser Phe Val Glu Val Glu Arg His Leu Glu
                 85                  90                  95

Cys Gly Cys Leu Ala Cys Ser
                100

<210> SEQ ID NO 7
<211> LENGTH: 1480
<212> TYPE: PRT
<213> ORGANISM: Drosophila melanogaster

<400> SEQUENCE: 7

Met Ala Ala Pro Ser Arg Thr Thr Leu Met Pro Pro Pro Phe Arg Leu
  1               5                  10                  15

Gln Leu Arg Leu Leu Ile Leu Pro Ile Leu Leu Leu Arg His Asp
                 20                  25                  30

Ala Val His Ala Glu Pro Tyr Ser Gly Gly Phe Gly Ser Ser Ala Val
             35                  40                  45

Ser Ser Gly Gly Leu Gly Ser Val Gly Ile His Ile Pro Gly Gly Gly
         50                  55                  60

Val Gly Val Ile Thr Glu Ala Arg Cys Pro Arg Val Cys Ser Cys Thr
 65                  70                  75                  80

Gly Leu Asn Val Asp Cys Ser His Arg Gly Leu Thr Ser Val Pro Arg
                 85                  90                  95

Lys Ile Ser Ala Asp Val Glu Arg Leu Glu Leu Gln Gly Asn Asn Leu
                100                 105                 110

Thr Val Ile Tyr Glu Thr Asp Phe Gln Arg Leu Thr Lys Leu Arg Met
            115                 120                 125

Leu Gln Leu Thr Asp Asn Gln Ile His Thr Ile Glu Arg Asn Ser Phe
        130                 135                 140

Gln Asp Leu Val Ser Leu Glu Arg Leu Asp Ile Ser Asn Asn Val Ile
145                 150                 155                 160

Thr Thr Val Gly Arg Arg Val Phe Lys Gly Ala Gln Ser Leu Arg Ser
                165                 170                 175

Leu Gln Leu Asp Asn Asn Gln Ile Thr Cys Leu Asp Glu His Ala Phe
            180                 185                 190

Lys Gly Leu Val Glu Leu Glu Ile Leu Thr Leu Asn Asn Asn Asn Leu
        195                 200                 205

Thr Ser Leu Pro His Asn Ile Phe Gly Gly Leu Gly Arg Leu Arg Ala
```

-continued

```
                210                 215                 220
Leu Arg Leu Ser Asp Asn Pro Phe Ala Cys Asp Cys His Leu Ser Trp
225                 230                 235                 240

Leu Ser Arg Phe Leu Arg Ser Ala Thr Arg Leu Ala Pro Tyr Thr Arg
                245                 250                 255

Cys Gln Ser Pro Ser Gln Leu Lys Gly Gln Asn Val Ala Asp Leu His
                260                 265                 270

Asp Gln Glu Phe Lys Cys Ser Gly Leu Thr Glu His Ala Pro Met Glu
                275                 280                 285

Cys Gly Ala Glu Asn Ser Cys Pro His Pro Cys Arg Cys Ala Asp Gly
290                 295                 300

Ile Val Asp Cys Arg Glu Lys Ser Leu Thr Ser Val Pro Val Thr Leu
305                 310                 315                 320

Pro Asp Asp Thr Thr Asp Val Arg Leu Glu Gln Asn Phe Ile Thr Glu
                325                 330                 335

Leu Pro Pro Lys Ser Phe Ser Phe Arg Arg Leu Arg Arg Ile Asp
                340                 345                 350

Leu Ser Asn Asn Asn Ile Ser Arg Ile Ala His Asp Ala Leu Ser Gly
                355                 360                 365

Leu Lys Gln Leu Thr Thr Leu Val Leu Tyr Gly Asn Lys Ile Lys Asp
                370                 375                 380

Leu Pro Ser Gly Val Phe Lys Gly Leu Gly Ser Leu Arg Leu Leu Leu
385                 390                 395                 400

Leu Asn Ala Asn Glu Ile Ser Cys Ile Arg Lys Asp Ala Phe Arg Asp
                405                 410                 415

Leu His Ser Leu Ser Leu Leu Ser Leu Tyr Asp Asn Asn Ile Gln Ser
                420                 425                 430

Leu Ala Asn Gly Thr Phe Asp Ala Met Lys Ser Met Lys Thr Val His
                435                 440                 445

Leu Ala Lys Asn Pro Phe Ile Cys Asp Cys Asn Leu Arg Trp Leu Ala
                450                 455                 460

Asp Tyr Leu His Lys Asn Pro Ile Glu Thr Ser Gly Ala Arg Cys Glu
465                 470                 475                 480

Ser Pro Lys Arg Met His Arg Arg Ile Glu Ser Leu Arg Glu Glu
                485                 490                 495

Lys Phe Lys Cys Ser Trp Gly Glu Leu Arg Met Lys Leu Ser Gly Glu
                500                 505                 510

Cys Arg Met Asp Ser Asp Cys Pro Ala Met Cys His Cys Glu Gly Thr
                515                 520                 525

Thr Val Asp Cys Thr Gly Arg Arg Leu Lys Glu Ile Pro Arg Asp Ile
                530                 535                 540

Pro Leu His Thr Thr Glu Leu Leu Asn Asp Asn Glu Leu Gly Arg
545                 550                 555                 560

Ile Ser Ser Asp Gly Leu Phe Gly Arg Leu Pro His Leu Val Lys Leu
                565                 570                 575

Glu Leu Lys Arg Asn Gln Leu Thr Gly Ile Glu Pro Asn Ala Phe Glu
                580                 585                 590

Gly Ala Ser His Ile Gln Glu Leu Gln Leu Gly Glu Asn Lys Ile Lys
                595                 600                 605

Glu Ile Ser Asn Lys Met Phe Leu Gly Leu His Gln Leu Lys Thr Leu
                610                 615                 620

Asn Leu Tyr Asp Asn Gln Ile Ser Cys Val Met Pro Gly Ser Phe Glu
625                 630                 635                 640
```

-continued

```
His Leu Asn Ser Leu Thr Ser Leu Asn Leu Ala Ser Asn Pro Phe Asn
                645                 650                 655

Cys Asn Cys His Leu Ala Trp Phe Ala Glu Cys Val Arg Lys Lys Ser
            660                 665                 670

Leu Asn Gly Gly Ala Ala Arg Cys Gly Ala Pro Ser Lys Val Arg Asp
        675                 680                 685

Val Gln Ile Lys Asp Leu Pro His Ser Glu Phe Lys Cys Ser Ser Glu
    690                 695                 700

Asn Ser Glu Gly Cys Leu Gly Asp Gly Tyr Cys Pro Pro Ser Cys Thr
705                 710                 715                 720

Cys Thr Gly Thr Val Val Ala Cys Ser Arg Asn Gln Leu Lys Glu Ile
                725                 730                 735

Pro Arg Gly Ile Pro Ala Glu Thr Ser Glu Leu Tyr Leu Glu Ser Asn
            740                 745                 750

Glu Ile Glu Gln Ile His Tyr Glu Arg Ile Arg His Leu Arg Ser Leu
        755                 760                 765

Thr Arg Leu Asp Leu Ser Asn Asn Gln Ile Thr Ile Leu Ser Asn Tyr
    770                 775                 780

Thr Phe Ala Asn Leu Thr Lys Leu Ser Thr Leu Ile Ile Ser Tyr Asn
785                 790                 795                 800

Lys Leu Gln Cys Leu Gln Arg His Ala Leu Ser Gly Leu Asn Asn Leu
                805                 810                 815

Arg Val Val Ser Leu His Gly Asn Arg Ile Ser Met Leu Pro Glu Gly
            820                 825                 830

Ser Phe Glu Asp Leu Lys Ser Leu Thr His Ile Ala Leu Gly Ser Asn
        835                 840                 845

Pro Leu Tyr Cys Asp Cys Gly Leu Lys Trp Phe Ser Asp Trp Ile Lys
    850                 855                 860

Leu Asp Tyr Val Glu Pro Gly Ile Ala Arg Cys Ala Glu Pro Glu Gln
865                 870                 875                 880

Met Lys Asp Lys Leu Ile Leu Ser Thr Pro Ser Ser Phe Val Cys
                885                 890                 895

Arg Gly Arg Val Arg Asn Asp Ile Leu Ala Lys Cys Asn Ala Cys Phe
            900                 905                 910

Glu Gln Pro Cys Gln Asn Gln Ala Gln Cys Val Ala Leu Pro Gln Arg
        915                 920                 925

Glu Tyr Gln Cys Leu Cys Gln Pro Gly Tyr His Gly Lys His Cys Glu
    930                 935                 940

Phe Met Ile Asp Ala Cys Tyr Gly Asn Pro Cys Arg Asn Asn Ala Thr
945                 950                 955                 960

Cys Thr Val Leu Glu Glu Gly Arg Phe Ser Cys Gln Cys Ala Pro Gly
                965                 970                 975

Tyr Thr Gly Ala Arg Cys Glu Thr Asn Ile Asp Asp Cys Leu Gly Glu
            980                 985                 990

Ile Lys Cys Gln Asn Asn Ala Thr Cys Ile Asp Gly Val Glu Ser Tyr
        995                 1000                1005

Lys Cys Glu Cys Gln Pro Gly Phe Ser Gly Glu Phe Cys Asp Thr Lys
    1010                1015                1020

Ile Gln Phe Cys Ser Pro Glu Phe Asn Pro Cys Ala Asn Gly Ala Lys
1025                1030                1035                1040

Cys Met Asp His Phe Thr His Tyr Ser Cys Asp Cys Gln Ala Gly Phe
                1045                1050                1055
```

-continued

```
His Gly Thr Asn Cys Thr Asp Asn Ile Asp Asp Cys Gln Asn His Met
        1060                1065                1070
Cys Gln Asn Gly Gly Thr Cys Val Asp Gly Ile Asn Asp Tyr Gln Cys
        1075                1080                1085
Arg Cys Pro Asp Asp Tyr Thr Gly Lys Tyr Cys Glu Gly His Asn Met
        1090                1095                1100
Ile Ser Met Met Tyr Pro Gln Thr Ser Pro Cys Gln Asn His Glu Cys
1105                1110                1115                1120
Lys His Gly Val Cys Phe Gln Pro Asn Ala Gln Gly Ser Asp Tyr Leu
                1125                1130                1135
Cys Arg Cys His Pro Gly Tyr Thr Gly Lys Trp Cys Glu Tyr Leu Thr
                1140                1145                1150
Ser Ile Ser Phe Val His Asn Asn Ser Phe Val Glu Leu Glu Pro Leu
        1155                1160                1165
Arg Thr Arg Pro Glu Ala Asn Val Thr Ile Val Phe Ser Ser Ala Glu
        1170                1175                1180
Gln Asn Gly Ile Leu Met Tyr Asp Gly Gln Asp Ala His Leu Ala Val
1185                1190                1195                1200
Glu Leu Phe Asn Gly Arg Ile Arg Val Ser Tyr Asp Val Gly Asn His
                1205                1210                1215
Pro Val Ser Thr Met Tyr Ser Phe Glu Met Val Ala Asp Gly Lys Tyr
        1220                1225                1230
His Ala Val Glu Leu Leu Ala Ile Lys Lys Asn Phe Thr Leu Arg Val
        1235                1240                1245
Asp Arg Gly Leu Ala Arg Ser Ile Ile Asn Glu Gly Ser Asn Asp Tyr
        1250                1255                1260
Leu Lys Leu Thr Thr Pro Met Phe Leu Gly Gly Leu Pro Val Asp Pro
1265                1270                1275                1280
Ala Gln Gln Ala Tyr Lys Asn Trp Gln Ile Arg Asn Leu Thr Ser Phe
                1285                1290                1295
Lys Gly Cys Met Lys Glu Val Trp Ile Asn His Lys Leu Val Asp Phe
        1300                1305                1310
Gly Asn Ala Gln Arg Gln Gln Lys Ile Thr Pro Gly Cys Ala Leu Leu
        1315                1320                1325
Glu Gly Glu Gln Gln Glu Glu Glu Asp Asp Glu Gln Asp Phe Met Asp
        1330                1335                1340
Glu Thr Pro His Ile Lys Glu Glu Pro Val Asp Pro Cys Leu Glu Asn
1345                1350                1355                1360
Lys Cys Arg Arg Gly Ser Arg Cys Val Pro Asn Ser Asn Ala Arg Asp
                1365                1370                1375
Gly Tyr Gln Cys Lys Cys His Gly Gln Arg Gly Arg Tyr Cys Asp
                1380                1385                1390
Gln Gly Glu Gly Ser Thr Glu Pro Pro Thr Val Thr Ala Ala Ser Thr
        1395                1400                1405
Cys Arg Lys Glu Gln Val Arg Glu Tyr Tyr Thr Glu Asn Asp Cys Arg
        1410                1415                1420
Ser Arg Gln Pro Leu Lys Tyr Ala Lys Cys Val Gly Gly Cys Gly Asn
1425                1430                1435                1440
Gln Cys Cys Ala Ala Lys Ile Val Arg Arg Arg Lys Val Arg Met Val
                1445                1450                1455
Cys Ser Asn Asn Arg Lys Tyr Ile Lys Asn Leu Asp Ile Val Arg Lys
        1460                1465                1470
Cys Gly Cys Thr Lys Lys Cys Tyr
```

```
                      1475                 1480

<210> SEQ ID NO 8
<211> LENGTH: 155
<212> TYPE: PRT
<213> ORGANISM: Caenorhabditis elegans
<220> FEATURE:
<221> NAME/KEY: misc_feature
<222> LOCATION: (4)..(152)
<223> OTHER INFORMATION: note="Xaa signifies gap in sequence"

<400> SEQUENCE: 8

Arg Asn Pro Xaa Ile Cys Asp Cys Asn Leu Gln Trp Leu Ala Gln Ile
 1               5                  10                  15

Asn Leu Gln Lys Asn Ile Glu Thr Ser Gly Ala Arg Cys Glu Gln Pro
            20                  25                  30

Lys Arg Leu Arg Lys Lys Phe Ala Thr Leu Pro Pro Asn Lys Phe
        35                  40                  45

Lys Cys Lys Gly Ser Glu Ser Phe Val Ser Met Tyr Ala Asp Ser Cys
    50                  55                  60

Phe Ile Asp Ser Ile Cys Pro Thr Gln Cys Asp Cys Tyr Gly Thr Thr
65                  70                  75                  80

Val Asp Cys Asn Lys Arg Gly Leu Asn Thr Ile Pro Thr Ser Ile Pro
                85                  90                  95

Arg Phe Ala Thr Gln Leu Leu Leu Ser Gly Asn Asn Ile Ser Thr Val
            100                 105                 110

Asp Leu Asn Ser Asn Ile His Val Leu Glu Asn Leu Glu Xaa Leu Asp
        115                 120                 125

Leu Ser Asn Asn His Ile Thr Phe Ile Asn Asp Lys Ser Phe Glu Lys
    130                 135                 140

Leu Ser Lys Leu Arg Glu Leu Xaa Leu Asn Asp
145                 150                 155

<210> SEQ ID NO 9
<211> LENGTH: 735
<212> TYPE: PRT
<213> ORGANISM: Caenorhabditis elegans

<400> SEQUENCE: 9

Ser Asn Lys Asn Leu Thr Ser Phe Pro Ser Arg Ile Pro Phe Asp Thr
 1               5                  10                  15

Thr Glu Leu Tyr Leu Asp Ala Asn Tyr Ile Asn Glu Ile Pro Ala His
            20                  25                  30

Asp Leu Asn Arg Leu Tyr Ser Leu Thr Lys Leu Asp Leu Ser His Asn
        35                  40                  45

Arg Leu Ile Ser Leu Glu Asn Asn Thr Phe Ser Asn Leu Thr Arg Leu
    50                  55                  60

Ser Thr Leu Ile Ile Ser Tyr Asn Lys Leu Arg Cys Leu Gln Pro Leu
65                  70                  75                  80

Ala Phe Asn Gly Leu Asn Ala Leu Arg Ile Leu Ser Leu His Gly Asn
                85                  90                  95

Asp Ile Ser Phe Leu Pro Gln Ser Ala Phe Ser Asn Leu Thr Ser Ile
            100                 105                 110

Thr His Ile Ala Val Gly Ser Asn Ser Leu Tyr Cys Asp Cys Asn Met
        115                 120                 125

Ala Trp Phe Ser Lys Trp Ile Lys Ser Lys Phe Ile Glu Ala Gly Ile
    130                 135                 140
```

-continued

```
Ala Arg Cys Glu Tyr Pro Asn Thr Val Ser Asn Gln Leu Leu Leu Thr
145                 150                 155                 160

Ala Gln Pro Tyr Gln Phe Thr Cys Asp Ser Lys Val Pro Thr Lys Leu
                165                 170                 175

Ala Thr Lys Cys Asp Leu Cys Leu Asn Ser Pro Cys Lys Asn Asn Ala
            180                 185                 190

Ile Cys Glu Thr Thr Ser Ser Arg Lys Tyr Thr Cys Asn Cys Thr Pro
        195                 200                 205

Gly Phe Tyr Gly Val His Cys Glu Asn Gln Ile Asp Ala Cys Tyr Gly
    210                 215                 220

Ser Pro Cys Leu Asn Asn Ala Thr Cys Lys Val Ala Gln Ala Gly Arg
225                 230                 235                 240

Phe Asn Cys Tyr Cys Asn Lys Gly Phe Glu Gly Asp Tyr Cys Glu Lys
                245                 250                 255

Asn Ile Asp Asp Cys Val Asn Ser Lys Cys Glu Asn Gly Gly Lys Cys
            260                 265                 270

Val Asp Leu Val Arg Phe Cys Ser Glu Glu Leu Lys Asn Phe Gln Ser
        275                 280                 285

Phe Gln Ile Asn Ser Tyr Arg Cys Asp Cys Pro Met Glu Tyr Glu Gly
    290                 295                 300

Lys His Cys Glu Asp Lys Leu Glu Tyr Cys Thr Lys Lys Leu Asn Pro
305                 310                 315                 320

Cys Glu Asn Asn Gly Lys Cys Ile Pro Ile Asn Gly Ser Tyr Ser Cys
                325                 330                 335

Met Cys Ser Pro Gly Phe Thr Gly Asn Asn Cys Glu Thr Asn Ile Asp
            340                 345                 350

Asp Cys Lys Asn Val Glu Cys Gln Asn Gly Gly Ser Cys Val Asp Gly
        355                 360                 365

Ile Leu Ser Tyr Asp Cys Leu Cys Arg Pro Gly Tyr Ala Gly Gln Tyr
    370                 375                 380

Cys Glu Ile Pro Pro Met Met Asp Met Glu Tyr Gln Lys Thr Asp Ala
385                 390                 395                 400

Cys Gln Gln Ser Ala Cys Gly Gln Gly Glu Cys Val Ala Ser Gln Asn
                405                 410                 415

Ser Ser Asp Phe Thr Cys Lys Cys His Glu Gly Phe Ser Gly Pro Ser
            420                 425                 430

Cys Asp Arg Gln Met Ser Val Gly Phe Lys Asn Pro Gly Ala Tyr Leu
        435                 440                 445

Ala Leu Asp Pro Leu Ala Ser Asp Gly Thr Ile Thr Met Thr Leu Arg
    450                 455                 460

Thr Thr Ser Lys Ile Gly Ile Leu Leu Tyr Tyr Gly Asp Asp His Phe
465                 470                 475                 480

Val Ser Ala Glu Leu Tyr Asp Gly Arg Val Lys Leu Val Tyr Tyr Ile
                485                 490                 495

Gly Asn Phe Pro Ala Ser His Met Tyr Ser Ser Val Lys Val Asn Asp
            500                 505                 510

Gly Leu Pro His Arg Ile Ser Ile Arg Thr Ser Glu Arg Lys Cys Phe
        515                 520                 525

Leu Gln Ile Asp Lys Asn Pro Val Gln Ile Val Glu Asn Ser Gly Lys
    530                 535                 540

Ser Asp Gln Leu Ile Thr Lys Gly Lys Glu Met Leu Tyr Ile Gly Gly
545                 550                 555                 560

Leu Pro Ile Glu Lys Ser Gln Asp Ala Lys Arg Arg Phe His Val Lys
```

```
                    565                 570                 575
Asn Ser Glu Ser Leu Lys Gly Cys Ile Ser Ser Ile Thr Ile Asn Glu
            580                 585                 590
Val Pro Ile Asn Leu Gln Gln Ala Leu Glu Asn Val Asn Thr Glu Gln
            595                 600                 605
Ser Cys Ser Ala Thr Val Asn Phe Cys Ala Gly Ile Asp Cys Gly Asn
            610                 615                 620
Gly Lys Cys Thr Asn Asn Ala Leu Ser Pro Lys Gly Tyr Met Cys Gln
625                 630                 635                 640
Cys Asp Ser His Phe Ser Gly Glu His Cys Asp Glu Lys Arg Ile Lys
                    645                 650                 655
Cys Asp Lys Gln Lys Phe Arg Arg His His Ile Glu Asn Glu Cys Arg
                660                 665                 670
Ser Val Asp Arg Ile Lys Ile Ala Glu Cys Asn Gly Tyr Cys Gly Gly
            675                 680                 685
Glu Gln Asn Cys Cys Thr Ala Val Lys Lys Lys Gln Arg Lys Val Lys
690                 695                 700
Met Ile Cys Lys Asn Gly Thr Thr Lys Ile Ser Thr Val His Ile Ile
705                 710                 715                 720
Arg Gln Cys Gln Cys Glu Pro Thr Lys Ser Val Leu Ser Glu Lys
                    725                 730                 735

<210> SEQ ID NO 10
<211> LENGTH: 154
<212> TYPE: PRT
<213> ORGANISM: mouse

<400> SEQUENCE: 10

Asp Pro Leu Pro Val His His Arg Cys Glu Cys Met Leu Gly Tyr Thr
1               5                   10                  15
Gly Asp Asn Cys Ser Glu Asn Gln Asp Asp Cys Lys Asp His Lys Cys
            20                  25                  30
Gln Asn Gly Ala Gln Cys Val Asp Glu Val Asn Ser Tyr Ala Cys Leu
        35                  40                  45
Cys Val Glu Gly Tyr Ser Gly Gln Leu Cys Glu Ile Pro Pro Ala Pro
    50                  55                  60
Arg Ser Ser Cys Glu Gly Thr Glu Cys Gln Asn Gly Ala Asn Cys Val
65                  70                  75                  80
Asp Gln Gly Ser Arg Pro Val Cys Gln Cys Leu Pro Gly Phe Gly Gly
                85                  90                  95
Pro Glu Cys Glu Lys Leu Leu Ser Val Asn Phe Val Asp Arg Asp Thr
            100                 105                 110
Tyr Leu Gln Phe Thr Asp Leu Gln Asn Trp Pro Arg Ala Asn Ile Thr
        115                 120                 125
Leu Gln Val Ser Thr Ala Glu Asp Asn Gly Ile Leu Leu Tyr Asn Gly
    130                 135                 140
Asp Asn Asp His Ile Ala Val Glu Leu Tyr
145                 150

<210> SEQ ID NO 11
<211> LENGTH: 110
<212> TYPE: PRT
<213> ORGANISM: mouse

<400> SEQUENCE: 11

Ala Phe Lys Cys His His Gly Gln Cys His Ile Ser Asp Arg Gly Glu
```

```
                1               5              10              15
Pro Tyr Cys Leu Cys Gln Pro Gly Phe Ser Gly His His Cys Glu Gln
                       20              25              30

Glu Asn Pro Cys Met Gly Glu Ile Val Arg Glu Ala Ile Arg Arg Gln
                35              40              45

Lys Asp Tyr Ala Ser Cys Ala Thr Ala Ser Lys Val Pro Ile Met Glu
        50              55              60

Cys Arg Gly Gly Cys Gly Thr Thr Cys Cys Gln Pro Ile Arg Ser Lys
 65              70              75              80

Arg Arg Lys Tyr Val Phe Gln Cys Thr Asp Gly Ser Ser Phe Val Glu
                    85              90              95

Glu Val Glu Arg His Leu Glu Cys Gly Cys Arg Ala Cys Ser
                100             105             110
```

<210> SEQ ID NO 12
<211> LENGTH: 134
<212> TYPE: PRT
<213> ORGANISM: mouse

<400> SEQUENCE: 12

```
His Leu Arg Val Leu Gln Leu Met Glu Asn Arg Ile Ser Thr Ile Glu
 1               5              10              15

Arg Gly Ala Phe Gln Asp Leu Lys Glu Leu Glu Arg Leu Arg Leu Asn
                20              25              30

Arg Asn Asn Leu Gln Leu Phe Pro Glu Leu Leu Phe Leu Gly Thr Ala
            35              40              45

Arg Leu Tyr Arg Leu Asp Leu Ser Glu Asn Gln Ile Gln Ala Ile Pro
     50              55              60

Arg Lys Ala Phe Arg Gly Ala Val Asp Ile Lys Asn Leu Gln Leu Asp
 65              70              75              80

Tyr Asn Gln Ile Ser Cys Ile Glu Asp Gly Ala Phe Arg Ala Leu Arg
                85              90              95

Asp Leu Glu Val Leu Thr Leu Asn Asn Asn Asn Ile Thr Arg Leu Ser
                100             105             110

Val Ala Ser Phe Asn His Met Pro Lys Leu Arg Thr Phe Arg Leu His
            115             120             125

Ser Asn Asn Leu Tyr Cys
     130
```

<210> SEQ ID NO 13
<211> LENGTH: 104
<212> TYPE: PRT
<213> ORGANISM: mouse

<400> SEQUENCE: 13

```
Asn Asn Asp Asp Cys Val Gly His Lys Cys Arg His Gly Ala Gln Cys
 1               5              10              15

Val Asp Glu Val Asn Gly Tyr Thr Cys Ile Cys Pro Gln Gly Phe Ser
                20              25              30

Gly Leu Phe Cys Glu His Pro Pro Met Val Leu Leu Gln Thr Ser
            35              40              45

Pro Cys Asp Gln Tyr Glu Cys Gln Asn Gly Ala Gln Cys Ile Val Val
     50              55              60

Gln Gln Glu Pro Thr Cys Arg Cys Pro Pro Gly Phe Ala Gly Pro Arg
 65              70              75              80

Cys Glu Lys Leu Ile Thr Val Asn Phe Val Gly Lys Asp Ser Tyr Val
```

Glu Leu Ala Ser Ala Lys Val Arg
                100

<210> SEQ ID NO 14
<211> LENGTH: 243
<212> TYPE: PRT
<213> ORGANISM: mouse

<400> SEQUENCE: 14

Ile Leu Asp Val Ala Ser Leu Arg Gln Ala Pro Gly Glu Asn Gly Thr
 1               5                  10                  15

Ser Phe His Gly Cys Ile Arg Asn Leu Tyr Ile Asn Ser Glu Leu Gln
                20                  25                  30

Asp Phe Arg Lys Met Pro Met Gln Thr Gly Ile Leu Pro Gly Cys Glu
            35                  40                  45

Pro Cys His Lys Lys Val Cys Ala His Gly Cys Cys Gln Pro Ser Ser
        50                  55                  60

Gln Ser Gly Phe Thr Cys Glu Cys Glu Glu Gly Trp Met Gly Pro Leu
 65                 70                  75                  80

Cys Asp Gln Arg Thr Asn Asp Pro Cys Leu Gly Asn Lys Cys Val His
                85                  90                  95

Gly Thr Cys Leu Pro Ile Asn Ala Phe Ser Tyr Ser Cys Lys Cys Leu
                100                 105                 110

Glu Gly His Gly Gly Val Leu Cys Asp Glu Glu Glu Asp Leu Phe Asn
            115                 120                 125

Pro Cys Gln Met Ile Lys Cys Lys His Gly Lys Cys Arg Leu Ser Gly
        130                 135                 140

Val Gly Gln Pro Tyr Cys Glu Cys Asn Ser Gly Phe Thr Gly Asp Ser
145                 150                 155                 160

Cys Asp Arg Glu Ile Ser Cys Arg Gly Glu Arg Ile Arg Asp Tyr Tyr
                165                 170                 175

Gln Lys Gln Gln Gly Tyr Ala Ala Cys Gln Thr Thr Lys Lys Val Ser
            180                 185                 190

Arg Leu Glu Cys Arg Gly Gly Cys Ala Gly Gly Gln Cys Cys Gly Pro
        195                 200                 205

Leu Arg Ser Lys Arg Arg Lys Tyr Ser Phe Glu Cys Thr Asp Gly Ser
        210                 215                 220

Ser Phe Val Asp Glu Val Glu Lys Val Val Lys Cys Gly Cys Ala Arg
225                 230                 235                 240

Cys Ala Ser

<210> SEQ ID NO 15
<211> LENGTH: 1395
<212> TYPE: PRT
<213> ORGANISM: Drosophila melanogaster

<400> SEQUENCE: 15

Met His Pro Met His Pro Glu Asn His Ala Ile Ala Arg Ser Thr Ser
 1               5                  10                  15

Thr Thr Asn Asn Pro Ser Arg Ser Arg Ser Arg Met Trp Leu Leu
                20                  25                  30

Pro Ala Trp Leu Leu Leu Val Leu Val Ala Ser Asn Gly Leu Pro Ala
            35                  40                  45

Val Arg Gly Gln Tyr Gln Ser Pro Arg Ile Ile Glu His Pro Thr Asp
        50                  55                  60

-continued

```
Leu Val Val Lys Lys Asn Glu Pro Ala Thr Leu Asn Cys Lys Val Glu
65                  70                  75                  80

Gly Lys Pro Glu Pro Thr Ile Glu Trp Phe Lys Asp Gly Glu Pro Val
                85                  90                  95

Ser Thr Asn Glu Lys Lys Ser His Arg Val Gln Phe Lys Asp Gly Ala
            100                 105                 110

Leu Phe Phe Tyr Arg Thr Met Gln Gly Lys Lys Glu Gln Asp Gly Gly
        115                 120                 125

Glu Tyr Trp Cys Val Ala Lys Asn Arg Val Gly Gln Ala Val Ser Arg
    130                 135                 140

His Ala Ser Leu Gln Ile Ala Val Leu Arg Asp Asp Phe Arg Val Glu
145                 150                 155                 160

Pro Lys Asp Thr Arg Val Ala Lys Gly Glu Thr Ala Leu Leu Glu Cys
                165                 170                 175

Gly Pro Pro Lys Gly Ile Pro Glu Pro Thr Leu Ile Trp Ile Lys Asp
            180                 185                 190

Gly Val Pro Leu Asp Asp Leu Lys Ala Met Ser Phe Gly Ala Ser Ser
        195                 200                 205

Arg Val Arg Ile Val Asp Gly Gly Asn Leu Leu Ile Ser Asn Val Glu
    210                 215                 220

Pro Ile Asp Glu Gly Asn Tyr Lys Cys Ile Ala Gln Asn Leu Val Gly
225                 230                 235                 240

Thr Arg Glu Ser Ser Tyr Ala Lys Leu Ile Val Gln Val Lys Pro Tyr
                245                 250                 255

Phe Met Lys Glu Pro Lys Asp Gln Val Met Leu Tyr Gly Gln Thr Ala
            260                 265                 270

Thr Phe His Cys Ser Val Gly Gly Asp Pro Pro Lys Val Leu Trp
        275                 280                 285

Lys Lys Glu Glu Gly Asn Ile Pro Val Ser Arg Ala Arg Ile Leu His
    290                 295                 300

Asp Glu Lys Ser Leu Glu Ile Ser Asn Ile Thr Pro Thr Asp Glu Gly
305                 310                 315                 320

Thr Tyr Val Cys Glu Ala His Asn Asn Val Gly Gln Ile Ser Ala Arg
                325                 330                 335

Ala Ser Leu Ile Val His Ala Pro Pro Asn Phe Thr Lys Arg Pro Ser
            340                 345                 350

Asn Lys Lys Val Gly Leu Asn Gly Val Val Gln Leu Pro Cys Met Ala
        355                 360                 365

Ser Gly Asn Pro Pro Ser Val Phe Trp Thr Lys Glu Gly Val Ser
    370                 375                 380

Thr Leu Met Phe Pro Asn Ser Ser His Gly Arg Gln Tyr Val Ala Ala
385                 390                 395                 400

Asp Gly Thr Leu Gln Ile Thr Asp Val Arg Gln Glu Asp Glu Gly Tyr
                405                 410                 415

Tyr Val Cys Ser Ala Phe Ser Val Val Asp Ser Ser Thr Val Arg Val
            420                 425                 430

Phe Leu Gln Val Ser Ser Val Asp Glu Arg Pro Pro Ile Ile Gln
        435                 440                 445

Ile Gly Pro Ala Asn Gln Thr Leu Pro Lys Gly Ser Val Ala Thr Leu
    450                 455                 460

Pro Cys Arg Ala Thr Gly Asn Pro Ser Pro Arg Ile Lys Trp Phe His
465                 470                 475                 480
```

```
Asp Gly His Ala Val Gln Ala Gly Asn Arg Tyr Ser Ile Ile Gln Gly
            485                 490                 495

Ser Ser Leu Arg Val Asp Asp Leu Gln Leu Ser Asp Ser Gly Thr Tyr
            500                 505                 510

Thr Cys Thr Ala Ser Gly Glu Arg Gly Glu Thr Ser Trp Ala Ala Thr
            515                 520                 525

Leu Thr Val Glu Lys Pro Gly Ser Thr Ser Leu His Arg Ala Ala Asp
            530                 535                 540

Pro Ser Thr Tyr Pro Ala Pro Pro Gly Thr Pro Lys Val Leu Asn Val
545                 550                 555                 560

Ser Arg Thr Ser Ile Ser Leu Arg Trp Ala Lys Ser Gln Glu Lys Pro
            565                 570                 575

Gly Ala Val Gly Pro Ile Ile Gly Tyr Thr Val Glu Tyr Phe Ser Pro
            580                 585                 590

Asp Leu Gln Thr Gly Trp Ile Val Ala Ala His Arg Val Gly Asp Thr
            595                 600                 605

Gln Val Thr Ile Ser Gly Leu Thr Pro Gly Thr Ser Tyr Val Phe Leu
            610                 615                 620

Val Arg Ala Glu Asn Thr Gln Gly Ile Ser Val Pro Ser Gly Leu Ser
625                 630                 635                 640

Asn Val Ile Lys Thr Ile Glu Ala Asp Phe Asp Ala Ala Ser Ala Asn
            645                 650                 655

Asp Leu Ser Ala Ala Arg Thr Leu Leu Thr Gly Lys Ser Val Glu Leu
            660                 665                 670

Ile Asp Ala Ser Ala Ile Asn Ala Ser Ala Val Arg Leu Glu Trp Met
            675                 680                 685

Leu His Val Ser Ala Asp Glu Lys Tyr Val Glu Gly Leu Arg Ile His
            690                 695                 700

Tyr Lys Asp Ala Ser Val Pro Ser Ala Gln Tyr His Ser Ile Thr Val
705                 710                 715                 720

Met Asp Ala Ser Ala Glu Ser Phe Val Val Gly Asn Leu Lys Lys Tyr
            725                 730                 735

Thr Lys Tyr Glu Phe Phe Leu Thr Pro Phe Phe Glu Thr Ile Glu Gly
            740                 745                 750

Gln Pro Ser Asn Ser Lys Thr Ala Leu Thr Tyr Glu Asp Val Pro Ser
            755                 760                 765

Ala Pro Pro Asp Asn Ile Gln Ile Gly Met Tyr Asn Gln Thr Ala Gly
770                 775                 780

Trp Val Arg Trp Thr Pro Pro Ser Gln His His Asn Gly Asn Leu
785                 790                 795                 800

Tyr Gly Tyr Lys Ile Glu Val Ser Ala Gly Asn Thr Met Lys Val Leu
            805                 810                 815

Ala Asn Met Thr Leu Asn Ala Thr Thr Thr Ser Val Leu Leu Asn Asn
            820                 825                 830

Leu Thr Thr Gly Ala Val Tyr Ser Val Arg Leu Asn Ser Phe Thr Lys
            835                 840                 845

Ala Gly Asp Gly Pro Tyr Ser Lys Pro Ile Ser Leu Phe Met Asp Pro
            850                 855                 860

Thr His His Val His Pro Pro Arg Ala His Pro Ser Gly Thr His Asp
865                 870                 875                 880

Gly Arg His Glu Gly Gln Asp Leu Thr Tyr His Asn Asn Gly Asn Ile
            885                 890                 895

Pro Pro Gly Asp Ile Asn Pro Thr Thr His Lys Lys Thr Thr Asp Tyr
```

-continued

```
                900             905             910
Leu Ser Gly Pro Trp Leu Met Val Leu Val Cys Ile Val Leu Val
        915                 920                 925
Leu Val Ile Ser Ala Ala Ile Ser Met Val Tyr Phe Lys Arg Lys His
        930                 935                 940
Gln Met Thr Lys Glu Leu Gly His Leu Ser Val Val Ser Asp Asn Glu
945                 950                 955                 960
Ile Thr Ala Leu Asn Ile Asn Ser Lys Glu Ser Leu Trp Ile Asp His
                965                 970                 975
His Arg Gly Trp Arg Thr Ala Asp Thr Asp Lys Asp Ser Gly Leu Ser
        980                 985                 990
Glu Ser Lys Leu Leu Ser His Val Asn Ser Ser Gln Ser Asn Tyr Asn
995                 1000                1005
Asn Ser Asp Gly Gly Thr Asp Tyr Ala Glu Val Asp Thr Arg Asn Leu
        1010                1015                1020
Thr Thr Phe Tyr Asn Cys Arg Lys Ser Pro Asp Asn Pro Thr Pro Tyr
1025                1030                1035                1040
Ala Thr Thr Met Ile Ile Gly Thr Ser Ser Glu Thr Cys Thr Lys
                1045                1050                1055
Thr Thr Ser Ile Ser Ala Asp Lys Asp Ser Gly Thr His Ser Pro Tyr
        1060                1065                1070
Ser Asp Ala Phe Ala Gly Gln Val Pro Ala Val Pro Val Val Lys Ser
        1075                1080                1085
Asn Tyr Leu Gln Tyr Pro Val Glu Pro Ile Asn Trp Ser Glu Phe Leu
        1090                1095                1100
Pro Pro Pro Pro Glu His Pro Pro Ser Ser Thr Tyr Gly Tyr Ala
1105                1110                1115                1120
Gln Gly Ser Pro Glu Ser Ser Arg Lys Ser Ser Lys Ser Ala Gly Ser
                1125                1130                1135
Gly Ile Ser Thr Asn Gln Ser Ile Leu Asn Ala Ser Ile His Ser Ser
                1140                1145                1150
Ser Ser Gly Gly Phe Ser Ala Trp Gly Val Ser Pro Gln Tyr Ala Val
        1155                1160                1165
Ala Cys Pro Pro Glu Asn Val Tyr Ser Asn Pro Leu Ser Ala Val Ala
        1170                1175                1180
Gly Gly Thr Gln Asn Arg Tyr Gln Ile Thr Pro Thr Asn Gln His Pro
1185                1190                1195                1200
Pro Gln Leu Pro Ala Tyr Phe Ala Thr Thr Gly Pro Gly Gly Ala Val
                1205                1210                1215
Pro Pro Asn His Leu Pro Phe Ala Thr Gln Arg His Ala Ala Ser Glu
                1220                1225                1230
Tyr Gln Ala Gly Leu Asn Ala Ala Arg Cys Ala Gln Ser Arg Ala Cys
        1235                1240                1245
Asn Ser Cys Asp Ala Leu Ala Thr Pro Ser Pro Met Gln Pro Pro Pro
        1250                1255                1260
Pro Val Pro Val Pro Glu Gly Trp Tyr Gln Pro Val His Pro Asn Ser
1265                1270                1275                1280
His Pro Met His Pro Thr Ser Ser Asn His Gln Ile Tyr Gln Cys Ser
                1285                1290                1295
Ser Glu Cys Ser Asp His Ser Arg Ser Ser Gln Ser His Lys Arg Gln
                1300                1305                1310
Leu Gln Leu Glu Glu His Gly Ser Ser Ala Lys Gln Arg Gly Gly His
        1315                1320                1325
```

His Arg Arg Arg Ala Pro Val Val Gln Pro Cys Met Glu Ser Glu Asn
    1330                1335                1340

Glu Asn Met Leu Ala Glu Tyr Glu Gln Arg Gln Tyr Thr Ser Asp Cys
1345                1350                1355                1360

Cys Asn Ser Ser Arg Glu Gly Asp Thr Cys Ser Cys Ser Glu Gly Ser
            1365                1370                1375

Cys Leu Tyr Ala Glu Ala Gly Glu Pro Ala Pro Arg Gln Met Thr Ala
            1380                1385                1390

Lys Asn Thr
    1395

<210> SEQ ID NO 16
<211> LENGTH: 1381
<212> TYPE: PRT
<213> ORGANISM: Drosophila melanogaster

<400> SEQUENCE: 16

Gly Glu Asn Pro Arg Ile Ile Glu His Pro Met Asp Thr Thr Val Pro
1               5                   10                  15

Lys Asn Asp Pro Phe Thr Phe Asn Cys Gln Ala Glu Gly Asn Pro Thr
            20                  25                  30

Pro Thr Ile Gln Trp Phe Lys Asp Gly Arg Glu Leu Lys Thr Asp Thr
        35                  40                  45

Gly Ser His Arg Ile Met Leu Pro Ala Gly Gly Leu Phe Phe Leu Lys
    50                  55                  60

Val Ile His Ser Arg Arg Glu Ser Asp Ala Gly Thr Tyr Trp Cys Glu
65                  70                  75                  80

Ala Lys Asn Glu Phe Gly Val Ala Arg Ser Arg Asn Ala Thr Leu Gln
                85                  90                  95

Val Ala Val Leu Arg Asp Glu Phe Arg Leu Glu Pro Ala Asn Thr Arg
            100                 105                 110

Val Ala Gln Gly Glu Val Ala Leu Met Glu Cys Gly Ala Pro Arg Gly
        115                 120                 125

Ser Pro Glu Pro Gln Ile Ser Trp Arg Lys Asn Gly Gln Thr Leu Asn
    130                 135                 140

Leu Val Gly Asn Lys Arg Ile Arg Ile Val Asp Gly Gly Asn Leu Ala
145                 150                 155                 160

Ile Gln Glu Ala Arg Gln Ser Asp Asp Gly Arg Tyr Gln Cys Val Val
                165                 170                 175

Lys Asn Val Val Gly Thr Arg Glu Ser Ala Thr Ala Phe Leu Lys Val
            180                 185                 190

His Val Arg Pro Phe Leu Ile Arg Gly Pro Gln Asn Gln Thr Ala Val
        195                 200                 205

Val Gly Ser Ser Val Val Phe Gln Cys Arg Ile Gly Gly Asp Pro Leu
    210                 215                 220

Pro Asp Val Leu Trp Arg Arg Thr Ala Ser Gly Gly Asn Met Pro Leu
225                 230                 235                 240

Arg Lys Phe Ser Trp Leu His Ser Ala Ser Gly Arg Val His Val Leu
                245                 250                 255

Glu Asp Arg Ser Leu Lys Leu Asp Asp Val Thr Leu Glu Asp Met Gly
            260                 265                 270

Glu Tyr Thr Cys Glu Ala Asp Asn Ala Val Gly Gly Ile Thr Ala Thr
        275                 280                 285

Gly Ile Leu Thr Val His Ala Pro Pro Lys Phe Val Ile Arg Pro Lys

```
                  290                 295                 300
Asn Gln Leu Val Glu Ile Gly Asp Glu Val Leu Phe Glu Cys Gln Ala
305                 310                 315                 320

Asn Gly His Pro Arg Pro Thr Leu Tyr Trp Ser Val Glu Gly Asn Ser
                325                 330                 335

Ser Leu Leu Pro Gly Tyr Arg Asp Gly Arg Met Glu Val Thr Leu
            340                 345                 350

Thr Pro Glu Gly Arg Ser Val Leu Ser Ile Ala Arg Phe Ala Arg Glu
                355                 360                 365

Asp Ser Gly Lys Val Val Thr Cys Asn Ala Leu Asn Ala Val Gly Ser
370                 375                 380

Val Ser Ser Arg Thr Val Val Ser Val Asp Thr Gln Phe Glu Leu Pro
385                 390                 395                 400

Pro Pro Ile Ile Glu Gln Gly Pro Val Asn Gln Thr Leu Pro Val Lys
                405                 410                 415

Ser Ile Val Val Leu Pro Cys Arg Thr Leu Gly Thr Pro Val Pro Gln
                420                 425                 430

Val Ser Trp Tyr Leu Asp Gly Ile Pro Ile Asp Val Gln Glu His Glu
            435                 440                 445

Arg Arg Asn Leu Ser Asp Ala Gly Ala Leu Thr Ile Ser Asp Leu Gln
450                 455                 460

Arg His Glu Asp Glu Gly Leu Tyr Thr Cys Val Ala Ser Asn Arg Asn
465                 470                 475                 480

Gly Lys Ser Ser Trp Ser Gly Tyr Leu Arg Leu Asp Thr Pro Thr Asn
                485                 490                 495

Pro Asn Ile Lys Phe Phe Arg Ala Pro Glu Leu Ser Thr Tyr Pro Gly
                500                 505                 510

Pro Pro Gly Lys Pro Gln Met Val Glu Lys Gly Glu Asn Ser Val Thr
                515                 520                 525

Leu Ser Trp Thr Arg Ser Asn Lys Val Gly Gly Ser Ser Leu Val Gly
                530                 535                 540

Tyr Val Ile Glu Met Phe Gly Lys Asn Glu Thr Asp Gly Trp Val Ala
545                 550                 555                 560

Val Gly Thr Arg Val Gln Asn Thr Thr Phe Thr Gln Thr Gly Leu Leu
                565                 570                 575

Pro Gly Val Asn Tyr Phe Leu Ile Arg Ala Glu Asn Ser His Gly
                580                 585                 590

Leu Ser Leu Pro Ser Pro Met Ser Glu Pro Ile Thr Val Gly Thr Arg
                595                 600                 605

Tyr Phe Asn Ser Gly Leu Asp Leu Ser Glu Ala Arg Ala Ser Leu Leu
            610                 615                 620

Ser Gly Asp Val Val Glu Leu Ser Asn Ala Ser Val Val Asp Ser Thr
625                 630                 635                 640

Ser Met Lys Leu Thr Trp Gln Ile Ile Asn Gly Lys Tyr Val Glu Gly
                645                 650                 655

Phe Tyr Val Tyr Ala Arg Gln Leu Pro Asn Pro Ile Val Asn Asn Pro
                660                 665                 670

Ala Pro Val Thr Ser Asn Thr Asn Pro Leu Leu Gly Ser Thr Ser Thr
                675                 680                 685

Ser Ala Ser Ala Ser Ala Ser Ala Leu Ile Ser Thr Lys Pro
            690                 695                 700

Asn Ile Ala Ala Ala Gly Lys Arg Asp Gly Glu Thr Asn Gln Ser Gly
705                 710                 715                 720
```

-continued

```
Gly Gly Ala Pro Thr Pro Leu Asn Thr Lys Tyr Arg Met Leu Thr Ile
            725                 730                 735
Leu Asn Gly Gly Gly Ala Ser Ser Cys Thr Ile Thr Gly Leu Val Gln
            740                 745                 750
Tyr Thr Leu Tyr Glu Phe Phe Ile Val Pro Phe Tyr Lys Ser Val Glu
            755                 760                 765
Gly Lys Pro Ser Asn Ser Arg Ile Ala Arg Thr Leu Glu Asp Val Pro
            770                 775                 780
Ser Glu Ala Pro Tyr Gly Met Glu Ala Leu Leu Leu Asn Ser Ser Ala
785                 790                 795                 800
Val Phe Leu Lys Trp Lys Ala Pro Glu Leu Lys Asp Arg His Gly Val
            805                 810                 815
Leu Leu Asn Tyr His Val Ile Val Arg Gly Ile Asp Thr Ala His Asn
            820                 825                 830
Phe Ser Arg Ile Leu Thr Asn Val Thr Ile Asp Ala Ala Ser Pro Thr
            835                 840                 845
Leu Val Leu Ala Asn Leu Thr Glu Gly Val Met Tyr Thr Val Gly Val
            850                 855                 860
Ala Ala Gly Asn Asn Ala Gly Val Gly Pro Tyr Cys Val Pro Ala Thr
865                 870                 875                 880
Leu Arg Leu Asp Pro Ile Thr Lys Arg Leu Asp Pro Phe Ile Asn Gln
            885                 890                 895
Arg Asp His Val Asn Asp Val Leu Thr Gln Pro Trp Phe Ile Ile Leu
            900                 905                 910
Leu Gly Ala Ile Leu Ala Val Leu Met Leu Ser Phe Gly Ala Met Val
            915                 920                 925
Phe Val Lys Arg Lys His Met Met Lys Gln Ser Ala Leu Asn Thr
            930                 935                 940
Met Arg Gly Asn His Thr Ser Asp Val Leu Lys Met Pro Ser Leu Ser
945                 950                 955                 960
Ala Arg Asn Gly Asn Gly Tyr Trp Leu Asp Ser Ser Thr Gly Gly Met
            965                 970                 975
Val Trp Arg Pro Ser Pro Gly Gly Asp Ser Leu Glu Met Gln Lys Asp
            980                 985                 990
His Ile Ala Asp Tyr Ala Pro Val Cys Gly Ala Pro Gly Ser Pro Ala
            995                 1000                1005
Gly Gly Gly Thr Ser Ser Gly Gly Ser Gly Ala Gly Ser Gly Ala
            1010                1015                1020
Ser Gly Gly Asp Asp Ile His Gly Gly His Gly Ser Glu Arg Asn Gln
1025                1030                1035                1040
Gln Arg Tyr Val Gly Glu Tyr Ser Asn Ile Pro Thr Asp Tyr Ala Glu
            1045                1050                1055
Val Ser Ser Phe Gly Lys Ala Pro Ser Glu Tyr Gly Arg His Gly Asn
            1060                1065                1070
Ala Ser Pro Ala Pro Tyr Ala Thr Ser Ser Ile Leu Ser Pro His Gln
            1075                1080                1085
Gln Gln Gln Gln Gln Gln Pro Arg Tyr Gln Arg Pro Val Pro Gly
            1090                1095                1100
Tyr Gly Leu Gln Arg Pro Met His Pro His Tyr Gln Gln Gln Gln His
1105                1110                1115                1120
Gln Gln Gln Gln Ala Gln Gln Thr His Gln Gln His Gln Ala Leu Gln
            1125                1130                1135
```

-continued

```
Gln His Gln Gln Leu Pro Pro Ser Asn Ile Tyr Gln Gln Met Ser Thr
            1140                1145                1150

Thr Ser Glu Ile Tyr Pro Thr Asn Thr Gly Pro Ser Arg Ser Val Tyr
        1155                1160                1165

Ser Glu Gln Tyr Tyr Pro Lys Asp Lys Gln Arg His Ile His Ile
    1170                1175                1180

Thr Glu Asn Lys Leu Ser Asn Cys His Thr Tyr Glu Ala Ala Pro Gly
1185                1190                1195                1200

Ala Lys Gln Ser Ser Pro Ile Ser Ser Gln Phe Ala Ser Val Arg Arg
            1205                1210                1215

Gln Gln Leu Pro Pro Asn Cys Ser Ile Gly Arg Glu Ser Ala Arg Phe
            1220                1225                1230

Lys Val Leu Asn Thr Asp Gln Gly Lys Asn Gln Gln Asn Leu Leu Asp
            1235                1240                1245

Leu Asp Gly Ser Ser Met Cys Tyr Asn Gly Leu Ala Asp Ser Gly Cys
1250                1255                1260

Gly Gly Ser Pro Ser Pro Met Ala Met Leu Met Ser His Glu Asp Glu
1265                1270                1275                1280

His Ala Leu Tyr His Thr Ala Asp Gly Asp Leu Asp Asp Met Glu Arg
            1285                1290                1295

Leu Tyr Val Lys Val Asp Glu Gln Gln Pro Pro Gln Gln Gln Gln
            1300                1305                1310

Leu Ile Pro Leu Val Pro Gln His Pro Ala Glu Gly His Leu Gln Ser
            1315                1320                1325

Trp Arg Asn Gln Ser Thr Arg Ser Ser Arg Lys Asn Gly Gln Glu Cys
            1330                1335                1340

Ile Lys Glu Pro Ser Glu Leu Ile Tyr Ala Pro Gly Ser Val Ala Ser
1345                1350                1355                1360

Glu Arg Ser Leu Leu Ser Asn Ser Gly Ser Gly Thr Ser Ser Gln Pro
            1365                1370                1375

Ala Gly His Asn Val
            1380

<210> SEQ ID NO 17
<211> LENGTH: 1297
<212> TYPE: PRT
<213> ORGANISM: Caenorhabditis elegans

<400> SEQUENCE: 17

Met Tyr Tyr Leu Gly Phe Tyr His Thr His Thr His Thr His Thr Tyr
1               5                   10                  15

Ile Asn Phe Asp Lys Ile Pro Asn Ala Ser Asn Leu Ala Pro Val Ile
            20                  25                  30

Ile Glu His Pro Ile Asp Val Val Ser Arg Gly Ser Pro Ala Thr
        35                  40                  45

Leu Asn Cys Gly Ala Lys Pro Ser Thr Ala Lys Ile Thr Trp Tyr Lys
    50                  55                  60

Asp Gly Gln Pro Val Ile Thr Asn Lys Glu Gln Val Asn Ser His Arg
65                  70                  75                  80

Ile Val Leu Asp Thr Gly Ser Leu Phe Leu Lys Val Asn Ser Gly
                85                  90                  95

Lys Asn Gly Lys Asp Ser Asp Ala Gly Ala Tyr Tyr Cys Val Ala Ser
            100                 105                 110

Asn Glu His Gly Glu Val Lys Ser Asn Glu Gly Ser Leu Lys Leu Ala
        115                 120                 125
```

```
Met Leu Arg Glu Asp Phe Arg Val Arg Pro Arg Thr Val Gln Ala Leu
    130                 135                 140
Gly Gly Glu Met Ala Val Leu Glu Cys Ser Pro Pro Arg Gly Phe Pro
145                 150                 155                 160
Glu Pro Val Val Ser Trp Arg Lys Asp Asp Lys Glu Leu Arg Ile Gln
                165                 170                 175
Asp Met Pro Arg Tyr Thr Leu His Ser Asp Gly Asn Leu Ile Ile Asp
            180                 185                 190
Pro Val Asp Arg Ser Asp Ser Gly Thr Tyr Gln Cys Val Ala Asn Asn
        195                 200                 205
Met Val Gly Glu Arg Val Ser Asn Pro Ala Arg Leu Ser Val Phe Glu
    210                 215                 220
Lys Pro Lys Phe Glu Gln Glu Pro Lys Asp Met Thr Val Asp Val Gly
225                 230                 235                 240
Ala Ala Val Leu Phe Asp Cys Arg Val Thr Gly Asp Pro Gln Pro Gln
                245                 250                 255
Ile Thr Trp Lys Arg Lys Asn Glu Pro Met Pro Val Thr Arg Ala Tyr
                260                 265                 270
Ile Ala Lys Asp Asn Arg Gly Leu Arg Ile Glu Arg Val Gln Pro Ser
            275                 280                 285
Asp Glu Gly Glu Tyr Val Cys Tyr Ala Arg Asn Pro Ala Gly Thr Leu
        290                 295                 300
Glu Ala Ser Ala His Leu Arg Val Gln Ala Pro Pro Ser Phe Gln Thr
305                 310                 315                 320
Lys Pro Ala Asp Gln Ser Val Pro Ala Gly Gly Thr Ala Thr Phe Glu
                325                 330                 335
Cys Thr Leu Val Gly Gln Pro Ser Pro Ala Tyr Phe Trp Ser Lys Glu
                340                 345                 350
Gly Gln Gln Asp Leu Leu Phe Pro Ser Tyr Val Ser Ala Asp Gly Arg
            355                 360                 365
Thr Lys Val Ser Pro Thr Gly Thr Leu Thr Ile Glu Glu Val Arg Gln
        370                 375                 380
Val Asp Glu Gly Ala Tyr Val Cys Ala Gly Met Asn Ser Ala Gly Ser
385                 390                 395                 400
Ser Leu Ser Lys Ala Ala Leu Lys Ala Thr Phe Glu Thr Lys Gly Arg
                405                 410                 415
Val Gln Lys Lys Lys Ser Lys Met Gly Lys Gln Lys Gln Lys Asn Val
                420                 425                 430
Gln Ser Ile Ile Lys Tyr Leu Ile Ser Ala Val Thr Gly Asn Thr Pro
            435                 440                 445
Ala Lys Pro Pro Pro Thr Ile Glu His Gly His Gln Asn Gln Thr Leu
        450                 455                 460
Met Val Gly Ser Ser Ala Ile Leu Pro Cys Gln Ala Ser Gly Lys Pro
465                 470                 475                 480
Thr Pro Gly Ile Ser Trp Leu Arg Asp Gly Leu Pro Ile Asp Ile Thr
                485                 490                 495
Asp Ser Arg Ile Ser Gln His Ser Thr Gly Ser Leu His Ile Ala Asp
            500                 505                 510
Leu Lys Lys Pro Asp Thr Gly Val Tyr Thr Cys Ile Ala Lys Asn Glu
        515                 520                 525
Asp Gly Glu Ser Thr Trp Ser Ala Ser Leu Thr Val Glu Asp His Thr
530                 535                 540
```

-continued

```
Ser Asn Ala Gln Phe Val Arg Met Pro Asp Pro Ser Asn Phe Pro Ser
545                 550                 555                 560

Ser Pro Thr Gln Pro Ile Ile Val Asn Val Thr Asp Thr Glu Val Glu
                565                 570                 575

Leu His Trp Asn Ala Pro Ser Thr Ser Gly Ala Gly Pro Ile Thr Gly
            580                 585                 590

Tyr Ile Ile Gln Tyr Tyr Ser Pro Asp Leu Gly Gln Thr Trp Phe Asn
        595                 600                 605

Ile Pro Asp Tyr Val Ala Ser Thr Glu Tyr Arg Ile Lys Gly Leu Lys
    610                 615                 620

Pro Ser His Ser Tyr Met Phe Val Ile Arg Ala Glu Asn Glu Lys Gly
625                 630                 635                 640

Ile Gly Thr Pro Ser Val Ser Ser Ala Leu Val Thr Thr Ser Lys Pro
                645                 650                 655

Ala Ala Gln Val Ala Leu Ser Asp Lys Asn Lys Met Asp Met Ala Ile
                660                 665                 670

Ala Glu Lys Arg Leu Thr Ser Glu Gln Leu Ile Lys Leu Glu Glu Val
            675                 680                 685

Lys Thr Ile Asn Ser Thr Ala Val Arg Leu Phe Trp Lys Lys Arg Lys
        690                 695                 700

Leu Glu Glu Leu Ile Asp Gly Tyr Tyr Ile Lys Trp Arg Gly Pro Pro
705                 710                 715                 720

Arg Thr Asn Asp Asn Gln Tyr Val Asn Val Thr Ser Pro Ser Thr Glu
                725                 730                 735

Asn Tyr Val Val Ser Asn Leu Met Pro Phe Thr Asn Tyr Glu Phe Phe
            740                 745                 750

Val Ile Pro Tyr His Ser Gly Val His Ser Ile His Gly Ala Pro Ser
        755                 760                 765

Asn Ser Met Asp Val Leu Thr Ala Glu Ala Pro Pro Ser Leu Pro Pro
770                 775                 780

Glu Asp Val Arg Ile Arg Met Leu Asn Leu Thr Thr Leu Arg Ile Ser
785                 790                 795                 800

Trp Lys Ala Pro Lys Ala Asp Gly Ile Asn Gly Ile Leu Lys Gly Phe
                805                 810                 815

Gln Ile Val Ile Val Gly Gln Ala Pro Asn Asn Asn Arg Asn Ile Thr
                820                 825                 830

Thr Asn Glu Arg Ala Ala Ser Val Thr Leu Phe His Leu Val Thr Gly
            835                 840                 845

Met Thr Tyr Lys Ile Arg Val Ala Ala Arg Ser Asn Gly Gly Val Gly
        850                 855                 860

Val Ser His Gly Thr Ser Glu Val Ile Met Asn Gln Asp Thr Leu Glu
865                 870                 875                 880

Lys His Leu Ala Ala Gln Gln Glu Asn Glu Ser Phe Leu Tyr Gly Leu
                885                 890                 895

Ile Asn Lys Ser His Val Pro Val Ile Val Ile Val Ala Ile Leu Ile
                900                 905                 910

Ile Phe Val Val Ile Ile Ile Ala Tyr Cys Tyr Trp Arg Asn Ser Arg
            915                 920                 925

Asn Ser Asp Gly Lys Asp Arg Ser Phe Ile Lys Ile Asn Asp Gly Ser
        930                 935                 940

Val His Met Ala Ser Asn Asn Leu Trp Asp Val Ala Gln Asn Pro Asn
945                 950                 955                 960

Gln Asn Pro Met Tyr Asn Thr Ala Gly Arg Met Thr Met Asn Asn Arg
```

-continued

```
                965                 970                 975
Asn Gly Gln Ala Leu Tyr Ser Leu Thr Pro Asn Ala Gln Asp Phe Phe
            980                 985                 990
Asn Asn Cys Asp Asp Tyr Ser Gly Thr Met His Arg Pro Gly Ser Glu
        995                1000                1005
His His Tyr His Tyr Ala Gln Leu Thr Gly Gly Pro Gly Asn Ala Met
    1010                1015                1020
Ser Thr Phe Tyr Gly Asn Gln Tyr His Asp Asp Pro Ser Pro Tyr Ala
1025                1030                1035                1040
Thr Thr Thr Leu Val Leu Ser Asn Gln Gln Pro Ala Trp Leu Asn Asp
            1045                1050                1055
Lys Met Leu Arg Ala Pro Ala Met Pro Thr Asn Pro Val Pro Pro Glu
                1060                1065                1070
Pro Pro Ala Arg Tyr Ala Asp His Thr Ala Gly Arg Arg Ser Arg Ser
            1075                1080                1085
Ser Arg Ala Ser Asp Gly Arg Gly Thr Leu Asn Gly Gly Leu His His
        1090                1095                1100
Arg Thr Ser Gly Ser Gln Arg Ser Asp Ser Pro Pro His Thr Asp Val
1105                1110                1115                1120
Ser Tyr Val Gln Leu His Ser Ser Asp Gly Thr Gly Ser Ser Lys Glu
                1125                1130                1135
Arg Thr Gly Glu Arg Arg Thr Pro Pro Asn Lys Thr Leu Met Asp Phe
            1140                1145                1150
Ile Pro Pro Pro Pro Ser Asn Pro Pro Pro Gly Gly His Val Tyr
        1155                1160                1165
Asp Thr Ala Thr Arg Arg Gln Leu Asn Arg Gly Ser Thr Pro Arg Glu
    1170                1175                1180
Asp Thr Tyr Asp Ser Val Ser Asp Gly Ala Phe Ala Arg Val Asp Val
1185                1190                1195                1200
Asn Ala Arg Pro Thr Ser Arg Asn Arg Asn Leu Gly Gly Arg Pro Leu
            1205                1210                1215
Lys Gly Lys Arg Asp Asp Asp Ser Gln Arg Ser Ser Leu Met Met Asp
        1220                1225                1230
Asp Asp Gly Gly Ser Ser Glu Ala Asp Gly Glu Asn Ser Glu Gly Asp
    1235                1240                1245
Val Pro Arg Gly Gly Val Arg Lys Ala Val Pro Arg Met Gly Ile Ser
1250                1255                1260
Ala Ser Thr Leu Ala His Ser Cys Tyr Gly Thr Asn Gly Thr Ala Gln
1265                1270                1275                1280
Arg Phe Arg Ser Ile Pro Arg Asn Asn Gly Ile Val Thr Gln Glu Gln
            1285                1290                1295
Thr

<210> SEQ ID NO 18
<211> LENGTH: 1651
<212> TYPE: PRT
<213> ORGANISM: human

<400> SEQUENCE: 18

Met Lys Trp Lys His Val Pro Phe Leu Val Met Ile Ser Leu Leu Ser
1               5                   10                  15
Leu Ser Pro Asn His Leu Phe Leu Ala Gln Leu Ile Pro Asp Pro Glu
            20                  25                  30
Asp Val Glu Arg Gly Asn Asp His Gly Thr Pro Ile Pro Thr Ser Asp
```

-continued

```
                35                  40                  45
Asn Asp Asp Asn Ser Leu Gly Tyr Thr Gly Ser Arg Leu Arg Gln Glu
         50                  55                  60

Asp Phe Pro Pro Arg Ile Val Glu His Pro Ser Asp Leu Ile Val Ser
 65                  70                  75                  80

Lys Gly Glu Pro Ala Thr Leu Asn Cys Lys Ala Glu Gly Arg Pro Thr
                 85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val
305                 310                 315                 320

Thr Ala Gly Asp Met Gly Ser Tyr Thr Cys Val Ala Glu Asn Met Val
                325                 330                 335

Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
        355                 360                 365

Thr Phe Gln Cys Glu Ala Thr Gly Asn Pro Gln Pro Ala Ile Phe Trp
    370                 375                 380

Arg Arg Glu Gly Ser Gln Asn Leu Leu Phe Ser Tyr Gln Pro Pro Gln
385                 390                 395                 400

Ser Ser Ser Arg Phe Ser Val Ser Gln Thr Gly Asp Leu Thr Ile Thr
                405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
        435                 440                 445

Ile Ala Asp Arg Pro Pro Val Ile Arg Gln Gly Pro Val Asn Gln
    450                 455                 460
```

-continued

```
Thr Val Ala Val Asp Gly Thr Phe Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
            500                 505                 510

Arg Tyr Ala Lys Leu Gly Asp Thr Gly Arg Tyr Thr Cys Ile Ala Ser
        515                 520                 525

Thr Pro Ser Gly Glu Ala Thr Trp Ser Ala Tyr Ile Glu Val Gln Glu
    530                 535                 540

Phe Gly Val Pro Val Gln Pro Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
            580                 585                 590

Ser Tyr Ile Ile Glu Ala Phe Ser His Ala Ser Gly Ser Ser Trp Gln
        595                 600                 605

Thr Val Ala Glu Asn Val Lys Thr Glu Thr Ser Ala Ile Lys Gly Leu
    610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
        675                 680                 685

Ser Ser Ile Glu Val His Trp Thr Val Asp Gln Gln Ser Gln Tyr Ile
    690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                725                 730                 735

Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
        755                 760                 765

Lys Thr Leu Glu Glu Ala Pro Ser Ala Pro Pro Gln Gly Val Thr Val
    770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
                805                 810                 815

Cys Leu Gly Asn Glu Thr Arg Tyr His Ile Asn Lys Thr Val Asp Gly
            820                 825                 830

Ser Thr Phe Ser Val Val Ile Pro Phe Leu Val Pro Gly Ile Arg Tyr
        835                 840                 845

Ser Val Glu Val Ala Ala Ser Thr Gly Ala Gly Ser Gly Val Lys Ser
    850                 855                 860

Glu Pro Gln Phe Ile Gln Leu Asp Ala His Gly Asn Pro Val Ser Pro
865                 870                 875                 880
```

-continued

Glu Asp Gln Val Ser Leu Ala Gln Gln Ile Ser Asp Val Val Lys Gln
            885                 890                 895

Pro Ala Phe Ile Ala Gly Ile Gly Ala Ala Cys Trp Ile Ile Leu Met
            900                 905                 910

Val Phe Ser Ile Trp Leu Tyr Arg His Arg Lys Lys Arg Asn Gly Leu
            915                 920                 925

Thr Ser Thr Tyr Ala Gly Ile Arg Lys Val Pro Ser Phe Thr Phe Thr
            930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
            965                 970                 975

Ala Asp Thr Trp Pro Asn Thr Gly Asn Asn His Asn Asp Cys Ser Ile
            980                 985                 990

Ser Cys Cys Thr Ala Gly Asn Gly Asn Ser Asp Ser Asn Leu Thr Thr
            995                 1000                1005

Tyr Ser Arg Pro Ala Asp Cys Ile Ala Asn Tyr Asn Asn Gln Leu Asp
            1010                1015                1020

Asn Lys Gln Thr Asn Leu Met Leu Pro Glu Ser Thr Val Tyr Gly Asp
1025                1030                1035                1040

Val Asp Leu Ser Asn Lys Ile Asn Glu Met Lys Thr Phe Asn Ser Pro
            1045                1050                1055

Asn Leu Lys Asp Gly Arg Phe Val Asn Pro Ser Gly Gln Pro Thr Pro
            1060                1065                1070

Tyr Ala Thr Thr Gln Leu Ile Gln Ser Asn Leu Ser Asn Asn Met Asn
            1075                1080                1085

Asn Gly Ser Gly Asp Ser Gly Glu Lys His Trp Lys Pro Leu Gly Gln
            1090                1095                1100

Gln Lys Gln Glu Val Ala Pro Val Gln Tyr Asn Ile Val Glu Gln Asn
1105                1110                1115                1120

Lys Leu Asn Lys Asp Tyr Arg Ala Asn Asp Thr Val Pro Pro Thr Ile
            1125                1130                1135

Pro Tyr Asn Gln Ser Tyr Asp Gln Asn Thr Gly Gly Ser Tyr Asn Ser
            1140                1145                1150

Ser Asp Arg Gly Ser Ser Thr Ser Gly Ser Gln Gly His Lys Lys Gly
            1155                1160                1165

Ala Arg Thr Pro Lys Val Pro Lys Gln Gly Gly Met Asn Trp Ala Asp
            1170                1175                1180

Leu Leu Pro Pro Pro Ala His Pro Pro His Ser Asn Ser Glu
1185                1190                1195                1200

Glu Tyr Asn Ile Ser Val Asp Glu Ser Tyr Asp Gln Glu Met Pro Cys
            1205                1210                1215

Pro Val Pro Pro Ala Arg Met Tyr Leu Gln Gln Asp Glu Leu Glu Glu
            1220                1225                1230

Glu Glu Asp Glu Arg Gly Pro Thr Pro Pro Val Arg Gly Ala Ala Ser
            1235                1240                1245

Ser Pro Ala Ala Val Ser Tyr Ser His Gln Ser Thr Ala Thr Leu Thr
            1250                1255                1260

Pro Ser Pro Gln Glu Glu Leu Gln Pro Met Leu Gln Asp Cys Pro Glu
1265                1270                1275                1280

Glu Thr Gly His Met Gln His Gln Pro Asp Arg Arg Gln Pro Val
            1285                1290                1295

Ser Pro Pro Pro Pro Pro Arg Pro Ile Ser Pro Pro His Thr Tyr Gly

-continued

```
                1300                1305                1310
Tyr Ile Ser Gly Pro Leu Val Ser Asp Met Asp Thr Asp Ala Pro Glu
        1315                1320                1325
Glu Glu Glu Asp Glu Ala Asp Met Glu Val Ala Lys Met Gln Thr Arg
    1330                1335                1340
Arg Leu Leu Leu Arg Gly Leu Glu Gln Thr Pro Ala Ser Ser Val Gly
1345                1350                1355                1360
Asp Leu Glu Ser Ser Val Thr Gly Ser Met Ile Asn Gly Trp Gly Ser
            1365                1370                1375
Ala Ser Glu Glu Asp Asn Ile Ser Ser Gly Arg Ser Ser Val Ser Ser
        1380                1385                1390
Ser Asp Gly Ser Phe Phe Thr Asp Ala Asp Phe Ala Gln Ala Val Ala
        1395                1400                1405
Ala Ala Ala Glu Tyr Ala Gly Leu Lys Val Ala Arg Arg Gln Met Gln
        1410                1415                1420
Asp Ala Ala Gly Arg Arg His Phe His Ala Ser Gln Cys Pro Arg Pro
1425                1430                1435                1440
Thr Ser Pro Val Ser Thr Asp Ser Asn Met Ser Ala Ala Val Met Gln
            1445                1450                1455
Lys Thr Arg Pro Ala Lys Lys Leu Lys His Gln Pro Gly His Leu Arg
        1460                1465                1470
Arg Glu Thr Tyr Thr Asp Asp Leu Pro Pro Pro Val Pro Pro Pro
        1475                1480                1485
Ala Ile Lys Ser Pro Thr Ala Gln Ser Lys Thr Gln Leu Glu Val Arg
        1490                1495                1500
Pro Val Val Pro Lys Leu Pro Ser Met Asp Ala Arg Thr Asp Arg
1505                1510                1515                1520
Ser Ser Asp Arg Lys Gly Ser Ser Tyr Lys Gly Arg Glu Val Leu Asp
            1525                1530                1535
Gly Arg Gln Val Val Asp Met Arg Thr Asn Pro Gly Asp Pro Arg Glu
        1540                1545                1550
Ala Gln Glu Gln Gln Asn Asp Gly Lys Gly Arg Gly Asn Lys Ala Ala
        1555                1560                1565
Lys Arg Asp Leu Pro Pro Ala Lys Thr His Leu Ile Gln Glu Asp Ile
1570                1575                1580
Leu Pro Tyr Cys Arg Pro Thr Phe Pro Thr Ser Asn Asn Pro Arg Asp
1585                1590                1595                1600
Pro Ser Ser Ser Ser Met Ser Ser Arg Gly Ser Gly Ser Arg Gln
            1605                1610                1615
Arg Glu Gln Ala Asn Val Gly Arg Arg Asn Ile Ala Glu Met Gln Val
        1620                1625                1630
Leu Gly Gly Tyr Glu Arg Gly Glu Asp Asn Asn Glu Glu Leu Glu Glu
        1635                1640                1645
Thr Glu Ser
    1650

<210> SEQ ID NO 19
<211> LENGTH: 434
<212> TYPE: PRT
<213> ORGANISM: human
<220> FEATURE:
<221> NAME/KEY: misc_feature
<222> LOCATION: (285)..(396)
<223> OTHER INFORMATION: note="Xaa signifies gap in sequence"

<400> SEQUENCE: 19
```

-continued

```
Gln Ile Val Ala Gln Gly Arg Thr Val Thr Phe Pro Cys Glu Thr Lys
 1               5                  10                  15

Gly Asn Pro Gln Pro Ala Val Phe Trp Gln Lys Glu Gly Ser Gln Asn
             20                  25                  30

Leu Leu Phe Pro Asn Gln Pro Gln Gln Pro Asn Ser Arg Cys Ser Val
         35                  40                  45

Ser Pro Thr Gly Asp Leu Thr Ile Thr Asn Ile Gln Arg Ser Asp Ala
     50                  55                  60

Gly Tyr Tyr Ile Cys Gln Ala Leu Thr Val Ala Gly Ser Ile Leu Ala
 65              70                  75                  80

Lys Ala Gln Leu Glu Val Thr Asp Val Leu Thr Asp Arg Pro Pro Pro
                 85                  90                  95

Ile Ile Leu Gln Gly Pro Ala Asn Gln Thr Leu Ala Val Asp Gly Thr
                100                 105                 110

Ala Leu Leu Lys Cys Lys Ala Thr Gly Asp Pro Leu Pro Val Ile Ser
            115                 120                 125

Trp Leu Lys Glu Gly Phe Thr Phe Pro Gly Arg Asp Pro Arg Ala Thr
130                 135                 140

Ile Gln Glu Gln Gly Thr Leu Gln Ile Lys Asn Leu Arg Ile Ser Asp
145                 150                 155                 160

Thr Gly Thr Tyr Thr Cys Val Ala Thr Ser Ser Gly Glu Ala Ser
                165                 170                 175

Trp Ser Ala Val Leu Asp Val Thr Glu Ser Gly Ala Thr Ile Ser Lys
            180                 185                 190

Asn Tyr Asp Leu Ser Asp Leu Pro Gly Pro Pro Ser Lys Pro Gln Val
            195                 200                 205

Thr Asp Val Thr Lys Asn Ser Val Thr Leu Ser Trp Gln Pro Gly Thr
        210                 215                 220

Pro Gly Thr Leu Pro Ala Ser Ala Tyr Ile Ile Glu Ala Phe Ser Gln
225                 230                 235                 240

Ser Val Ser Asn Ser Trp Gln Thr Val Ala Asn His Val Lys Thr Thr
                245                 250                 255

Leu Tyr Thr Val Arg Gly Leu Arg Pro Asn Thr Ile Tyr Leu Phe Met
                260                 265                 270

Val Arg Ala Ile Asn Pro Lys Val Ser Val Thr Gln Xaa Lys Pro Gln
            275                 280                 285

Lys Asn Asn Gly Ser Thr Trp Ala Asn Val Pro Leu Pro Pro Pro Pro
            290                 295                 300

Val Gln Pro Leu Pro Gly Thr Glu Leu Glu His Tyr Ala Val Glu Gln
305                 310                 315                 320

Gln Glu Asn Gly Tyr Asp Ser Asp Ser Trp Cys Pro Pro Leu Pro Val
                325                 330                 335

Gln Thr Tyr Leu His Gln Gly Leu Glu Asp Glu Leu Glu Glu Asp Asp
            340                 345                 350

Asp Arg Val Pro Thr Pro Pro Val Arg Gly Val Ala Ser Ser Pro Ala
        355                 360                 365

Ile Ser Phe Gly Gln Gln Ser Thr Ala Thr Leu Thr Pro Ser Pro Arg
    370                 375                 380

Glu Glu Met Gln Pro Met Leu Gln Ala Ser Pro Xaa Phe Thr Ser Ser
385                 390                 395                 400

Gln Arg Pro Arg Pro Thr Ser Pro Phe Ser Thr Asp Ser Asn Thr Ser
                405                 410                 415
```

-continued

```
Ala Ala Leu Ser Gln Ser Gln Arg Pro Arg Pro Thr Lys Lys His Lys
            420                 425                 430

Gly Gly

<210> SEQ ID NO 20
<211> LENGTH: 148
<212> TYPE: PRT
<213> ORGANISM: mouse

<400> SEQUENCE: 20

Ala Gln Ala Val Ala Ala Ala Glu Tyr Ala Gly Leu Lys Val Ala
1               5                   10                  15

Arg Arg Gln Met Gln Asp Ala Ala Gly Arg Arg His Phe His Ala Ser
                20                  25                  30

Gln Cys Pro Arg Pro Thr Ser Pro Val Ser Thr Asp Ser Asn Met Ser
            35                  40                  45

Ala Val Val Ile Gln Lys Ala Arg Pro Ala Lys Lys Gln Lys His Gln
    50                  55                  60

Pro Gly His Leu Arg Arg Glu Ala Tyr Ala Asp Asp Leu Pro Pro Pro
65              70                  75                  80

Pro Val Pro Pro Pro Ala Ile Lys Ser Pro Thr Val Gln Ser Lys Ala
                85                  90                  95

Gln Leu Glu Val Arg Pro Val Met Val Pro Lys Leu Ala Ser Ile Glu
                100                 105                 110

Ala Arg Thr Asp Arg Ser Ser Asp Arg Lys Gly Gly Ser Tyr Lys Gly
            115                 120                 125

Arg Glu Ala Leu Asp Gly Arg Gln Val Thr Asp Leu Arg Thr Asn Pro
        130                 135                 140

Ser Asp Pro Arg
145
```